United States Patent [19]
Atkinson

[11] Patent Number: 5,742,054
[45] Date of Patent: Apr. 21, 1998

[54] ULTRA-SENSITIVE DETECTION OF CONTAMINANTS IN CORROSIVE GAS VIA INTRACAVITY LASER SPECTROSCOPY (ILS)

[75] Inventor: George H. Atkinson, Tucson, Ariz.

[73] Assignee: Innovative Lasers Corporation, Tucson, Ariz.

[21] Appl. No.: 675,554

[22] Filed: Jul. 3, 1996

Related U.S. Application Data

[63] Continuation-in-part of Ser. No. 522,963, Sep. 1, 1995, Pat. No. 5,689,334.
[51] Int. Cl.$^6$ .................................................. G01J 3/02
[52] U.S. Cl. ....................... 250/339.13; 250/343; 356/439
[58] Field of Search .............................. 250/339.13, 343; 372/41; 356/300, 436–440

[56] References Cited

U.S. PATENT DOCUMENTS

| | | | |
|---|---|---|---|
| 4,648,714 | 3/1987 | Benner et al. | 356/301 |
| 5,432,610 | 7/1995 | King et al. | 356/432 |

OTHER PUBLICATIONS

Kachanov et al, "Intracavity Laser Spectroscopy with Vibronic Solid–State Lasers. I. Spectrotemporal Transient Behavior of a Ti: Sapphire Laser", J. Opt. Soc. Am B, vol. 11, Dec. 12, 1994.

G. Atkinson et al, "Detection of Free Radicals by an Intracavity Dye Laser Technique," 59 *Journal Of Chemical Physics*, Jul. 1, 1973.

D. Gilmore et al, "Intracavity Absorption spectroscopy With a Titanium: Sapphire Laser," *Optics Communications* 77 (1990) 385–89.

G. Atkinson, "Intracavity Laser Spectroscopy," SPIE Conf., *Soc. Opt. Eng.* 1637 (1992).

D. Gilmore et al, "Intracavity Laser Spectroscopy in the 1.38–1.55 µm Spectral Region Using a Multimode $Cr^{4+}$: YAG Laser," *Optics Communications* 103 (1993) 370–74.

Purchase Orders: No. 7L–M0508, dated Nov. 15, 1995, and Nov. 29, 1995.

Quotation submitted to a potential customer, Sep. 2, 1994.

G.H. Atkinson et al, "Quantitative Intracavity Laser Detection of $NO_2$ by Optical Multichannel Analysis," Journal of Chemical Physics, vol. 66, No. 11, pp. 5005–5012 (Jun. 1, 1977).

N. Goldstein et al, "Quantitative Absorption Spectroscopy of $NO_2$ in a Supersonically Cooled Jet by Intracavity Laser Techniques," Chemical Physics Letters, vol. 116, No. 2,3, pp. 223–230 (May 3, 1985).

G.H. Atkinson, "High Sensitivity, Time–Resolved Absorption Spectroscopy by Intracavity Laser Techniques," in Advances in Chemical Reaction Dynamics, P. Rentzepis and C. Capellos, eds., Nato ASI Series C. vol. 184, D. Reidel Publishing Company, Boston, 1986, pp. 207–228.

N. Goldstein et al, "Quantitative Absorption Spectroscopy of Dissociation Dynamics of $I_2$ Van der Waals Complexes with He, Ar, Kr, and Xe," Journal of Chemical Physics, vol. 85, No. 5, pp. 2684–2691 (Sep. 1, 1986).

(List continued on next page.)

*Primary Examiner*—Michael J. Tokar
*Assistant Examiner*—Richard Hanig
*Attorney, Agent, or Firm*—Benman & Collins

[57] ABSTRACT

Contaminants in corrosive gases are detected optically at concentrations below 1 part-per-million (ppm) and extending to a level below 1 part-per-billion (ppb) by using intracavity laser spectroscopy (ILS) techniques. A laser, the ILS laser, is employed as a detector. The ILS laser comprises a gain medium contained in a laser cavity. A gas sample containing gaseous contaminant species is contained within a gas sample cell which is placed inside the laser cavity and on one side of the gain medium. Accordingly, the corrosive gas is prevented from reacting with the components of the ILS laser. The output signal from the ILS laser is detected and analyzed to identify the gaseous species (via its spectral signature). The concentration of the gaseous species can be determined from the spectral signature as well.

18 Claims, 8 Drawing Sheets

OTHER PUBLICATIONS

J.J. O'Brien et al, "Detection of the $SiH_2$ Radical by Intracavity Laser Spectroscopy," Analysis, vol. 16, No. 9–10, pp. 34–40 (1988).

A. Campargue et al, "High Sensitivity Intracavity Laser Spectroscopy: Applications to the Study of Overtone Transitions in the Visible Range," Spectrochimica Acta Review, vol. 13, No. 1, pp. 69–88 (1990).

A. Campargue et al, "Intracavity Laser Absorption Spectroscopy of $NO_2$ and $CH_4$ Cooled in a Split Jet Supersonic Expansion," Journal de Physique IV, vol. 1, pp. 471–476 (Dec. 1991).

Q. Zhu et al, "A High Resolution Spectroscopic Study of $SiH_4$ $\mu$= 6 and 7 Overtones," Spectrochimica Acta, vol. 50A, No. 4, pp. 663–670 (1994).

B.B. Radak et al, "Line Intensities in the 647.5–nm Ammonia Band at Low Temperatures Determined by Intracavity Laser Spectroscopy," Journal of Quantum Spectroscopy and Radiative Transfer, vol. 53, No. 5, pp. 519–526 (1995).

ULTRA-SENSITIVE DETECTION OF CONTAMINANTS IN CORROSIVE GAS VIA INTRACAVITY LASER SPECTROSCOPY (ILS)

CROSS-REFERENCE TO RELATED APPLICATION

This application is a continuation-in-part of application Ser. No. 08/522,963 filed on Sep. 1, 1995 now U.S. Pat. No. 5,689,334.

This application is related to the application Ser. No. 08/675,605 filed on even date herewith. That application concerns an ILS laser pumped with a semiconductor diode laser. The present application is directed to a method for detecting the presence of gaseous species in a gas sample containing corrosive gas.

TECHNICAL FIELD

This invention relates, generally, to the detection of contaminants in gases, and more particularly, to the high sensitivity detection of gaseous molecules, atoms, radicals, and/or ions by laser techniques generally termed intracavity laser spectroscopy (ILS).

BACKGROUND OF THE INVENTION

In the preparation of high quality semiconductor material (e.g., silicon films) for use in the microelectronics industry, it is well known that contaminants must be controlled. Failure to control contaminants, as is also well known and appreciated, can result in the loss of significant resources as the resultant products are typically not useful for their intended purposes.

Generally, the starting materials in the fabrication of silicon films consist essentially of gases, typically denoted either "bulk" (e.g., nitrogen or argon) or "specialty" (e.g., hydrogen chloride, hydrogen bromide, boron trichloride). The successful operation of a fabrication facility designed to prepare semiconductor materials depends directly on the purity of the starting gases, as well as the gas handling capabilities available to preserve gas purity during the delivery of the gases to the process chamber and while material processing is taking place. Suitable control of the purity of such starting gases (i.e., monitoring and inhibiting high levels of contaminants as may be contained in the gases) is essential.

Under many current techniques, such control is achieved after the fact. That is, the silicon films so produced are periodically tested and the production line shut down only after such tests reveal the presence of high level contaminants. These processes, as will be appreciated by those skilled in the art, can lead to the waste of not only starting materials but also product which is produced prior to cessation of production. It is therefore desirable to monitor and control the contaminants as may be contained in such starting gases during production so as unacceptable contaminant levels are observed, production can be immediately, or at least shortly thereafter, halted.

Many molecular, atomic, radical, and ionic species are present in the bulk and specialty gases used in the preparation (e.g., chemical vapor deposition or "CVD") and processing (doping and etching) of semiconductor materials that can be viewed as "contaminants." Such contaminants can degrade either the quality of the fabricated semiconductor material or the efficiency with which the semiconductor material is prepared. These contaminant species can interfere with the chemical process directly or even cause particles to be formed in the gas delivery lines or process chamber which subsequently deposit on the surface of the wafer material causing indirect performance defects.

The first step in controlling and/or eliminating these contaminants is their detection in the bulk and specialty gases used as starting materials. While this is generally recognized, heretofore practiced methods are generally inadequate. This is due, in large part, to the situation created by seemingly ever increasing competitive industry standards which have developed. Specifically, as the size of microelectronic devices has decreased while performance specifications have been intensified, the requirements for gas purity (i.e., absence of microcontamination) has increased.

Against this backdrop, it will likely be clear that several measurement criteria are important to detector effectiveness: (1) absolute detection sensitivity usually stated as parts-per-total number of gas molecules in the sample (e.g., parts-per-million or number of contaminant molecules per $10^{+6}$ background molecules); (2) species selectivity or the capability to measure the concentration of one species in the presence of other species; (3) rapidity of measurements to obtain a desired signal to noise ratio; (4) capability of monitoring contaminants in both non-reactive and reactive gases; and (5) linearity and dynamic range of gas concentrations that can be measured.

The current state-of-the-art devices for contaminant detection (e.g., water) encompass a variety of measurement techniques. For example, current state-of-the-art devices for water vapor detection utilize conductivity and electrochemical, direct absorption spectroscopy, and atmospheric pressure ionization mass spectroscopy (APIMS) measurement techniques. As discussed below, each of these methods fails to adequately address these requirements.

Conductivity and Electrochemical

Conductivity and electrochemical methods by solid-state devices exist which can detect water vapor at the 1 to 100 ppm range. Conductivity and electrochemical methods generally require direct physical contact between the sample and the device; thus, detection occurs after water molecules deposit on the solid-state surface. As a consequence, these devices do not perform well, if at all, with utilization of reactive or corrosive gases. In such corrosive environments, the performance lifetimes of these devices are limited since the materials from which they are fabricated deteriorate in the presence of the corrosive sample being measured. The need to have direct contact with the sample is a major limitation since it is unlikely that a particular material can perform well and resist deterioration over extended use. Indeed, even their performance in non-reactive gases changes and/or deteriorates after even short exposures to reactive or corrosive gases. The linearity and dynamic range of response are usually limited to about one decade. The detection selectivity of these devices with respect to different gaseous species also is generally poor since the devices themselves will respond to a wide range of species without discrimination. Additionally, selectivity is incorporated into the measurements only through whatever chemical selectivity, if any, is embodied in the coatings used to cover these devices.

Direct Absorption

Direct absorption spectroscopy generally relates to the passing of light through the sample from an external source and measuring the reduction in light intensity caused by molecular, atomic, radical, and/or ionic absorption in the sample. Detection sensitivity depends directly on the subtraction of two large numbers (light intensity from the external source before it passes through the sample and its intensity after it exits the sample). This limits the detection sensitivity to the extent that direct absorption is generally considered a low sensitivity methodology.

APIMS

APIMS, initially used in the analysis of impurities in bulk nitrogen and argon and ambient air for air pollution studies, is now currently used by semiconductor manufacturers to detect trace levels of moisture and oxygen in inert bulk gases. With APIMS, the sampled gas is bombarded with electrons, or may be flame and photon excited, to produce a variety of ions that are then detected directly. Particularly, ionization occurs at atmospheric pressure in the presence of a reagent gas in the ionization source. APIMS typically exhibits detection sensitivities in the range of about 10 parts per trillion (ppt) in non-reactive gases. APIMS cannot even be used with reactive or corrosive gas mixtures. Additional disadvantages of APIMS include an average cost between about $150,000 to $250,000, extensive purging and calibration procedures, and the need for a knowledgeable operator.

Intracavity Laser Spectroscopy

In the context of the present invention, laser technology, specifically intracavity laser spectroscopy (ILS), is disclosed as being used as a detector (sensor) to detect gaseous species (contaminants) at very high sensitivity levels. While the methods and apparatus disclosed herein are particularly suited for application in fabrication of semiconductor components, it should be appreciated that the present invention in its broadest form is not so limited. Nevertheless, for convenience of reference and description of preferred exemplary embodiments, this application will be used as a benchmark. In connection with this application, laser technology offers distinct advantages to gaseous species (contaminant) detection over known methods and, particularly, to water vapor detection.

In conventional applications of lasers to the detection of gaseous species (contaminants), laser produced radiation is used to excite the gas sample external to the laser in order to produce a secondary signal (e.g., ionization or fluorescence). Alternatively, the intensity of the laser after it passes through a gas sample, normalized to its initial intensity, can be measured (i.e., absorption).

Some twenty years ago, another detection methodology, intracavity laser spectroscopy, was first explored in which the laser itself is used as a detector; see, e.g., G. Atkinson, A. Laufer, M. Kurylo, "Detection of Free Radicals by an Intracavity Dye Laser Technique," 59 *Journal Of Chemical Physics*, Jul. 1, 1973.

Intracavity laser spectroscopy (ILS) combines the advantages of conventional absorption spectroscopy with the high detection sensitivity normally associated with other laser techniques such as laser-induced fluorescence (LIF) and multiphoton ionization (MPI) spectroscopy. ILS is based on the intracavity losses associated with absorption in gaseous species (e.g., atoms, molecules, radicals, or ions) found within the optical resonator cavity of a multimode, homogeneously broadened laser. These intracavity absorption losses compete via the normal mode dynamics of a multimode laser with the gain generated in the laser medium (i.e., gain medium). Traditionally, ILS research has been dominated by the use of dye lasers because their multimode properties fulfill the conditions required for effective mode competition and their wide tunability provides spectral access to many different gaseous species. Some ILS experiments have been performed with multimode, tunable solid-state laser media such as color centers and Ti:Sapphire; see, e.g., D. Gilmore, P. Cvijin, G. Atkinson, "Intracavity Absorption Spectroscopy With a Titanium: Sapphire Laser," *Optics Communications* 77 (1990) 385–89.

ILS has also been successfully used to detect both stable and transient species under experimental conditions where the need for high detection sensitivity had previously excluded absorption spectroscopy as a method of choice. For example, ILS has been utilized to examine gaseous samples in environments such as cryogenically cooled chambers, plasma discharges, photolytic and pyrolytic decompositions, and supersonic jet expansions. ILS has been further used to obtain quantitative absorption information (e.g., line strengths and collisional broadening coefficients) through the analysis of absorption lineshapes. Some of these are described in G. Atkinson, "Intracavity Laser Spectroscopy," SPIE Conf., *Soc. Opt. Eng.* 1637 (1992).

Prior art methods of performing ILS, however, while suitable for use in laboratory settings, are unacceptable for commercial settings. The constraints of commercial reality, as briefly noted above, essentially dictate that such a detector be conveniently sized, relatively inexpensive, and reliable. Laboratory models fail to fully meet these requirements.

Additionally, in the commercial setting for which ILS detection can be applied, the gas sample may be contained in an environment which is not ideal. In particular, for industrial processes, the gas sample is commonly contained in corrosive gas. For example, in the manufacture of semiconductor components, the ability to detect the presence of a contaminant (such as water vapor) in the presence of a corrosive gas (such as hydrogen chloride) would be particularly useful.

A laboratory demonstration of the feasibility of using ILS techniques for detecting small quantities of water vapor in a nitrogen atmosphere with a $Cr^{4+}$:YAG laser is described in D. Gilmore, P. Cvijin, G. Atkinson, "Intracavity Laser Spectroscopy in the 1.38–1.55 μm Spectral Region Using a Multimode $Cr^{4+}$:YAG Laser," *Optics Communications* 103 (1993) 370–74. The experimental apparatus utilized was satisfactory for demonstration of operational characteristics, but undesirable for implementation in a commercial application as contemplated by the present invention, in particular, for the detection of water vapor in a corrosive gas such as hydrogen chloride (HCl).

In accordance with various aspects of the present invention, the present invention provides a user friendly, i.e., comparatively simple, detection system, having the advantages of direct absorption techniques but with dramatically increased detection sensitivities, capable of detecting gaseous species in corrosive samples at a commercially viable cost. In this regard, the present invention addresses the long felt need for a method and apparatus for the high sensitivity detection of contaminants in corrosive gas systems in commercial settings.

SUMMARY OF THE INVENTION

In accordance with the present invention, a method is provided for detecting the presence of gaseous species in a gas sample containing corrosive gas. The method comprises:

(a) selecting a spectral region wherein (i) the gaseous species has at least one absorption feature and (ii) the corrosive gas has essentially no absorption features;

(b) providing a laser comprising a laser cavity and a gain medium which resides therein, the gain medium outputting light having a wavelength distribution at least a portion of which is in the selected spectral region;

(c) providing a gas sample cell having windows which are transparent to light in the selected spectral region such that a beam of light can pass through the gas sample cell;

(d) inserting the gas sample cell in the laser such that output light from the gain medium passes through the gas sample prior to exiting the laser cavity;

(e) inserting the gas sample containing the corrosive gas in the gas sample cell such that output light from the gain medium passes through the gas sample, the gas sample sealed within the gas sample cell such that the corrosive gas does not react with the laser; and (f) directing the output beam of the gain medium after exiting the laser cavity to a detector assembly for determining the presence and/or concentration of the gaseous species in the gas sample.

The ILS gas detection system of the present invention preferably comprises a pumping laser used to provide the optical excitement required to operate the ILS laser, a multimode ILS laser operated over the wavelength region in which the species of interest absorbs, a gas sample cell placed within the optical resonator cavity of the ILS laser to contain the corrosive gas, a wavelength dispersive spectrometer capable of spectrally resolving the output of the ILS laser, a detector capable of measuring the wavelength-resolved intensity of the ILS laser output, and an electronic circuit which can read the signal from the detector and convert it into electronic signal that can be processed by a computer. The ILS gas detection system may also include a chopping, pulsing, or modulating device designed to periodically interrupt the intensity of the pumping laser beam and the output from the ILS laser.

In accordance with various aspects of the present invention, contaminants are detected optically at concentrations below 1 part-per-million (ppm) and extending to a level below 1 part-per-billion (ppb) by using ILS techniques. For detecting water vapor in HCl, a solid-state laser with an ion-doped crystal medium and operating in the 1300 nm to 1500 nm spectral region preferably serves as the detector. A gas sample containing gaseous contaminant species (water vapor) and corrosive gas (HCl) is placed inside the optical resonator cavity of the laser (between reflective surfaces or mirrors) and on one side of the active medium. Laser media having $Cr^{4+}$:YAG and $Cr^{4+}$:LuAG are described here, but other gain mediums such as other ion-doped crystals having multiple longitudinal and transverse cavity modes can be used as well. Alternative lasers systems may be employed as well. For example, a diode laser pumped solid state laser with an ion-doped crystal medium may be optically configured to provide ILS detection.

BRIEF DESCRIPTION OF THE DRAWINGS

Preferred exemplary embodiments of the present invention will be hereinafter described in conjunction with the appended drawing figures, wherein like designations denote like elements. The drawings referred to in this description should be understood as not being drawn to scale except if specifically noted.

FIG. 1A shows the basic configuration, while FIG. 1B shows that configuration as embodied in an exemplary embodiment shown in FIG. 2;

DESCRIPTION OF THE PREFERRED EMBODIMENTS

Reference is now made in detail to a specific embodiment of the present invention, which illustrates the best mode presently contemplated by the inventor for practicing the invention. Alternative embodiments are also briefly described as applicable.

As previously briefly noted, the subject matter of the present invention is particularly well suited for use in connection with the manufacture of semiconductor components, and thus, a preferred exemplary embodiment of the present invention will be described in that context. It should be recognized, however, that such description is not intended as a limitation on the use or applicability of the subject invention, but rather is set forth to merely fully describe a preferred exemplary embodiment thereof.

In this regard, the present invention is particularly suited for detection of contaminants. Contaminants as used herein refers to molecular, atomic, radical, and ionic species such as may be present in gaseous materials, such as in the gaseous materials which are used in the fabrication of silicon films, i.e., inlet lines. Alternatively, the term contaminant may also refer to the gaseous material itself, such as, for example when the detector of the present invention is used to determine if a line (e.g., HCl line) has been sufficiently purged of the gaseous material.

Figure 1A:
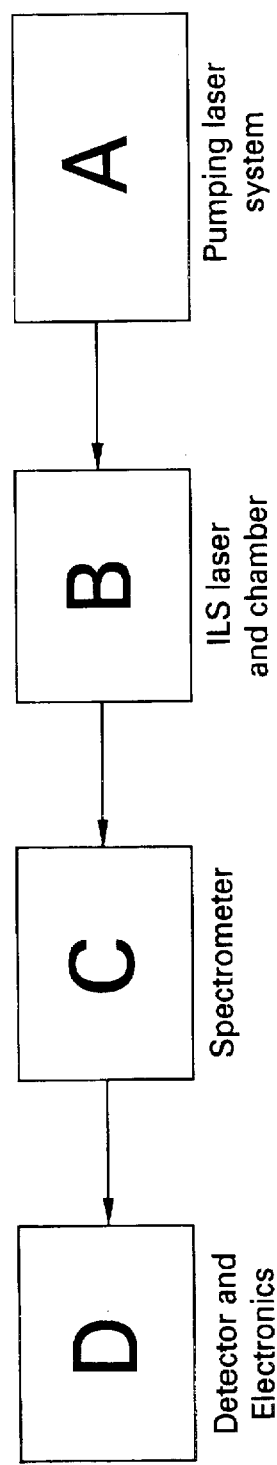
FIGS. 1A and 1B are schematic block diagrams of a contaminant detector system in accordance with the present invention.
Figure 1B:
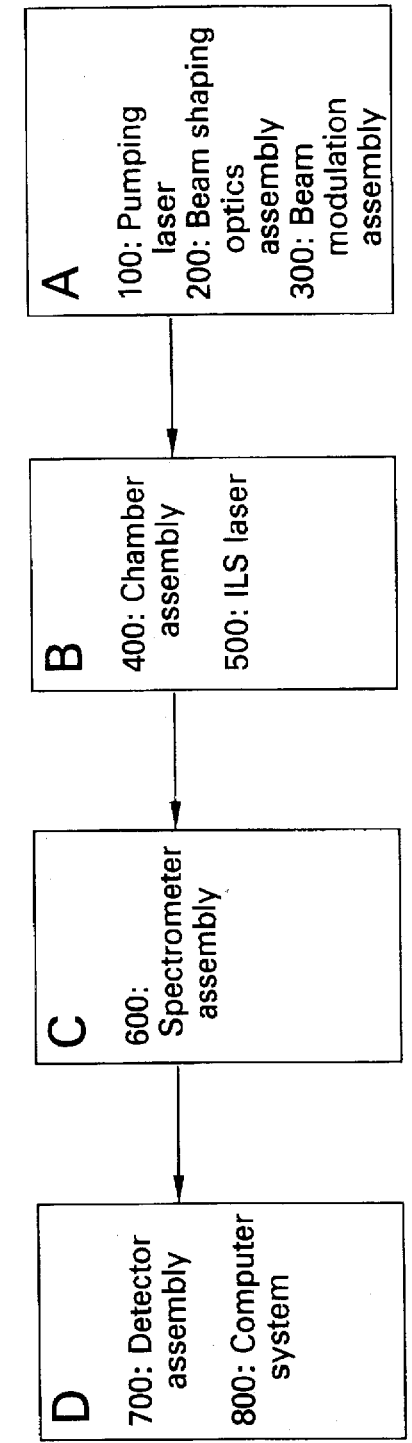

In accordance with a preferred embodiment of the present invention and with momentary reference to FIG. 1A, a gas (contaminant) detection system 10 suitably comprises a pumping laser system A, an ILS laser and associated chamber B, a spectrometer C, and a detector with associated electronics (e.g., computer, digital electronics, etc.) D. More particularly, and with reference to FIGS. 1B and 2, pumping laser system A suitably comprises a pumping laser 100, a beam shaping optics assembly 200 and a beam modulation assembly 300; laser and chamber B suitably comprises a chamber assembly 400 and an ILS laser 500; spectrometer C suitably comprises a spectrometer assembly 600; and, detector D suitably comprises a detector assembly 700 and a computer system 800. As will be described more fully herein, gas detection system 10 advantageously detects gaseous species (contaminants) which are suitably contained in a gas sample. In general, pumping laser driver system A pumps ILS laser 500, preferably at or near the threshold level such that a laser beam passes through the gas sample thereby enabling the spectrum of the gas sample to be obtained. This spectrum is suitably detected through use of detector/computer system D which, upon manipulation, enables the reliable and accurate determination of the presence and concentration at high sensitivity levels of gaseous species (contaminants) which may be contained within the gas sample.

Figure 3:
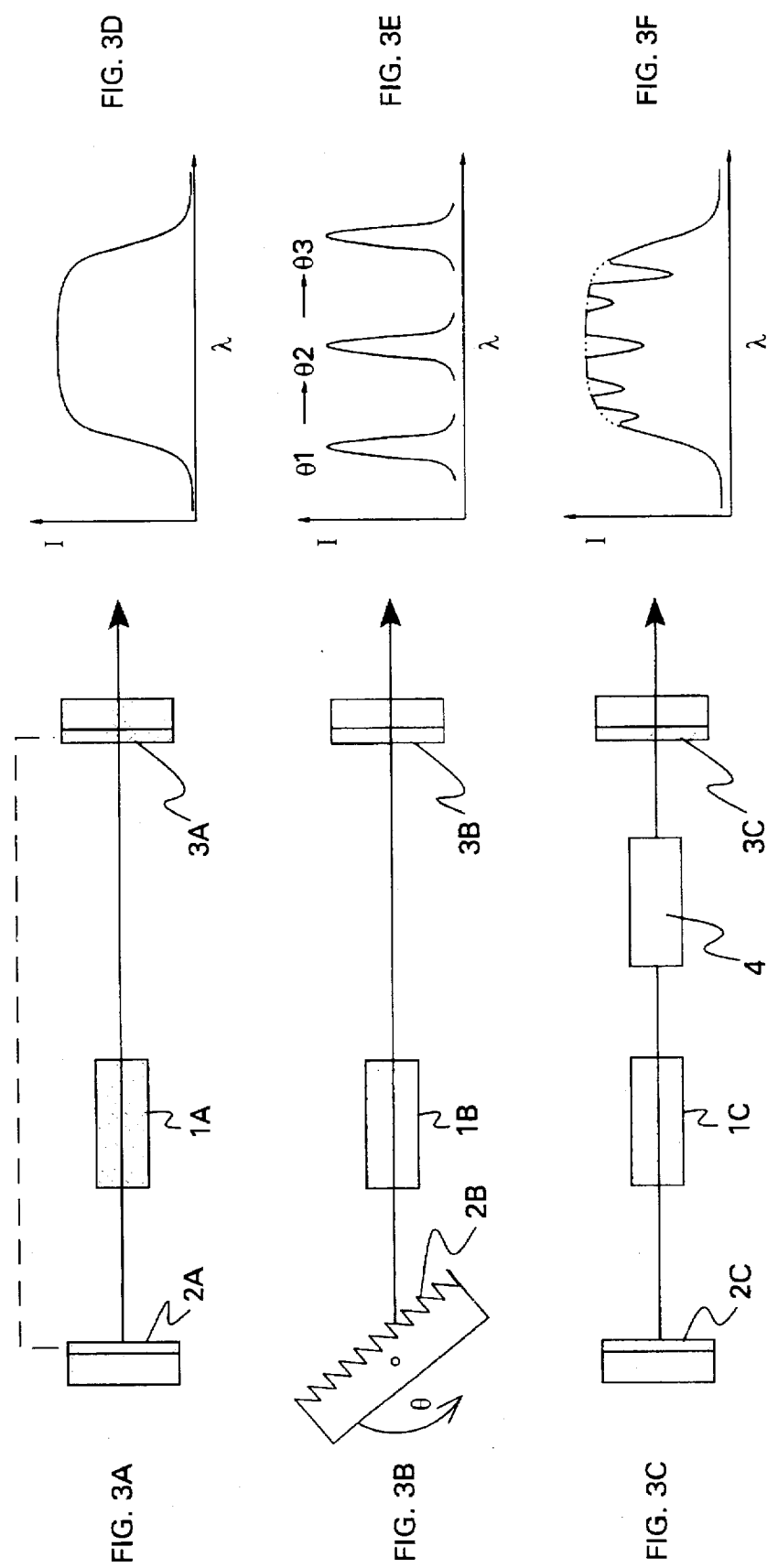
FIGS. 3A–3C include schematic representations of simple laser devices.
FIGS. 3D–3F are graphs that represent the graphical spectral outputs (intensity versus wavelength) obtainable from the devices depicted in FIGS. 3A–3C, respectively.

With reference to FIGS. 3A–3C, and in order to more fully explain the scientific principles utilized in accordance with a preferred embodiment of the present invention, the general principles of intracavity laser spectroscopy (ILS) are illustratively shown. As is known, in its simplest terms, a laser can be described as containing a gain medium, in which optical gain is produced, and a resonator, comprised of optical elements such as mirrors. Optical losses may appear in both the gain medium and the optical elements comprising the laser cavity (e.g., the resonator). With particular reference to FIG. 3A, a laser device in its simplest form can be schematically illustrated as including a gain medium 1A around which respective mirrors 2A and 3A are placed. Mirrors 2A and 3A are typically coated to have high reflectivity surfaces over a broad spectral range. For example, the mirror coating on mirror 2A may be totally reflective, while the mirror coating on mirror 3A may be partially reflective thereby permitting some light to escape from the laser cavity. The spatial region between the reflective surfaces of mirrors 2A and 3A in which the gain medium 1A is placed defines the laser resonator or cavity, and in the context of the present invention relates to the so-called "intracavity region."

The intensity (I) of the laser output may be determined both by the wavelength region over which the gain medium 1A operates ($\lambda$) and the reflectivity of the resonator elements (e.g., mirrors 2A and 3A). Normally this output is broad and without sharp, distinctive spectral features, as is shown in the plot of I versus wavelength ($\lambda$) provided in FIG. 3D, which corresponds to the laser of FIG. 3A.

By selecting different optical elements to form the laser cavity, the spectral output of the laser can be altered or "tuned." For example, and with particular reference to FIG. 3B, a tuned resonator cavity may include a diffraction grating 2B which replaces the highly reflective mirror 2A shown in FIG. 3A. As shown, the laser device therefore includes diffraction grating 2B, mirror 3B, and a gain medium 1B positioned therebetween. In general, the result in spectral output from this tuned laser will be narrowed and appear as wavelengths within the original spectral output of the laser defined by the gained medium 1A and the mirrors 2A and 3A (FIG. 10A). For example, a schematic plot of intensity (I) versus wavelength ($\lambda$) illustrating a narrowed output is depicted in FIG. 3E.

The laser output can also be altered by placing gaseous molecules, atoms, radicals, and/or ions in either their ground or excited states inside the optical resonator (e.g., cavity). With reference to FIG. 3C, a laser so configured may include a highly reflective minor 2C, a partially reflective mirror 3C with a gain medium 1C, and an intracavity absorber 4 placed therebetween. In this case, intracavity absorber 4 may comprise such gaseous species (e.g., the sample containing contaminants). The effect of the intracavity gaseous species on the laser output can be observed. For example, a plot of I versus $\lambda$ for such a device is shown in FIG. 3F. FIG. 3F comprises an absorption spectrum of the gaseous species contained within intracavity absorber 4. The distinct absorption features illustrated in FIG. 3F arise from the intracavity species losses against which the laser gain must compete.

Thus, the absorption spectrum of the intracavity species may appear in the spectral output of the laser. In particular, the laser output intensity (I) at wavelengths where the stronger intracavity absorption features compete effectively against the gain properties of the resonator are more reduced. As a result, as illustrated, instead of a relatively smooth continuous output, such as shown in FIG. 3D, a structured laser output such as shown in FIG. 3F may be observed. The decreases in intensity (I), as shown in FIG. 3F, are due to absorption by the gaseous intracavity species, i.e., the more intense the absorption features, the larger the decrease in the laser output intensity. In accordance with the present invention, the absorption spectrum obtained by intracavity laser measurements in which an intracavity absorber is employed can be utilized for the high sensitivity detection of such gaseous species. It has been found that each gaseous species can be uniquely identified by its respective absorption spectrum (signature) and thus can be used to confidently identify such gaseous species (contaminant).

The present inventor has found that the appearance of the absorbing species (gaseous elements) within the laser resonator before and/or during the competition between gain and losses which naturally occur as the laser system approaches threshold give rise to enhanced detection sensitivity through use of ILS. In view of the fact that the losses associated with the intracavity absorber become part of the competition between the gain and losses within the laser, even a small absorbance associated either with a weak absorption transition and/or an extremely small absorber concentration is amplified dramatically during the gain/loss competition. As a result, such competition dearly appears in the output of the ILS signal (see FIG. 3F). Thus, using these principles, ILS can be utilized to detect both weak absorption and/or extremely small absorber concentrations.

ILS detection differs significantly from other spectroscopy methods which employ lasers. As described above, the output of a laser used for spectroscopy typically excites in a gaseous species, a secondary phenomena which is then monitored. Alternatively, output of a laser may be passed through a gaseous species and the absorption of selected wavelengths in the output of the laser provides means for characterizing the gas. In either case, the operation of the laser is separate from and unaffected by the gaseous species being measured.

With ILS detection, however, the operation of the laser is directly affected by the gaseous species. In this manner, the ILS laser 500 itself acts as a detector. In particular, the output from the ILS laser 500 as it exits the laser cavity contains spectroscopic information about the gaseous species. This mode of operation is unique to ILS detection and the ILS laser 500.

Accordingly, ILS lasers 500 are distinctly different from conventional lasers and possess operational characteristics which are not typical of conventional lasers. For example, absorbing species which produce loss are intentionally introduced into the laser cavity of ILS lasers 500. These absorbing species affect the operation of the ILS laser 500 and alter its output.

Also, unlike lasers employed in conventional applications, ILS lasers 500 operate above but close to threshold (e.g., within 10% of threshold power). However, operating near threshold often causes the output of the ILS laser 500 to be unstable. Accordingly, additional techniques directed to stabilizing the output of the ILS laser 500 may be required.

In contrast, conventional lasers typically operate well above threshold to maximize output. Maximizing output, however, is not the objective of ILS lasers 500. Consequently, laser media which are inefficient and/or do not produce high output power may be employed for ILS detection when such laser media are unfavorable for most other laser applications. The purpose of the ILS laser 500 is not to produce light, but to monitor loss within the laser cavity. As described above, mode competition inside the laser cavity enables such loss within the ILS laser 500 to be detected with enhanced sensitivity.

Since ILS detection possesses increased sensitivity beyond conventional optical spectroscopy techniques, interferences from background gases having both weak absorption and/or extremely small absorber concentrations may be significant, even if such interferences are negligible with conventional spectroscopy techniques.

The detection of gases via ILS can be achieved by using a variety of laser systems. (As used herein, the laser system includes both the ILS laser 500 and the pump laser 100). These laser systems each share several common properties which are required for extremely high detection sensitivity. Prior art has identified three such properties. First, the laser systems exhibit multimode operation near the energy threshold for lasing. Second, the laser systems possess an operational wavelength bandwidth that is substantially broad relative to the absorption features of the gaseous species or contaminants (i.e., molecules, atoms, radicals, and/or ions) being monitored. Third, the laser systems maintain stable intensity and wavelength.

It will be appreciated that a variety of ILS laser systems having different physical and optical characteristics meet these above-listed criteria for extremely high detection sensitivity. The different physical and optical characteristics of the laser systems may also provide distinct advantages such as with regard to the experimental conditions (e.g., data acquisition times) under which ILS measurements are made. Additionally, these different physical and optical characteristics may influence one or more of the following: (1) the gaseous species or contaminant (i.e., molecules, atoms, radicals, and/or ions) that can be detected; (2) the respective concentrations of each gaseous species that can be determined; and (3) the practical types of samples to which detection can be applied. Examples of the latter include the total pressure of the sample, the sample size, and the environment within which the sample is contained.

Against the backdrop of these general principles, in the context of the present invention, the present inventor has devised a commercially viable contaminant sensor system 10 which provides enhanced detection of contaminants in gaseous samples which contain corrosive gases (i.e., gases which react with the components comprising the ILS laser 500).

Figure 2:
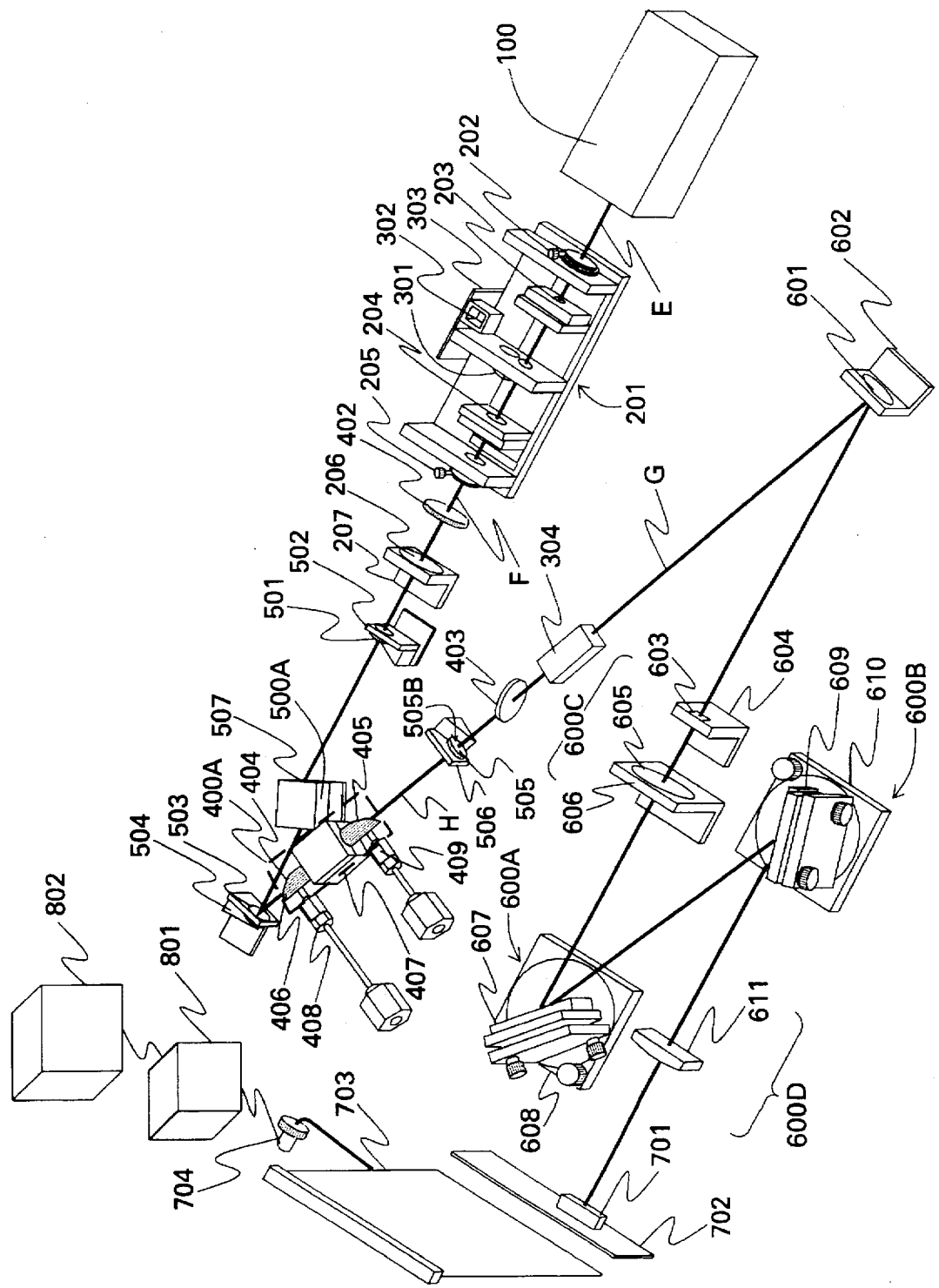
FIG. 2 is a more detailed schematic perspective view of the exemplary embodiment of a contaminant detector system in accordance with the present invention.

With reference now to FIGS. 1A and 2, and in accordance with a preferred exemplary embodiment of the present invention, a gas detection system 10 suitably includes laser driver 100 and an ILS chamber assembly 400 in which ILS laser 500 is contained. Spectrometer assembly 600 and a detector/computer system 700, 800 are suitably optically connected to the output from ILS laser 500 whereat the absorption spectrum is suitably manipulated thus enabling the high sensitivity detection of the presence and/or concentration of gaseous species (contaminants).

The ILS laser 500 operates in a wavelength region or spectral region suitable for detection of the contaminant contained within the gas sample (e.g., water vapor). Within this spectral region a signature absorption spectrum can be obtained. Since gas phase spectroscopy has been studied extensively, a large and directly useful literature exists which shows how gaseous species can be uniquely identified.

It will be appreciated that ILS detection can be used to monitor one gaseous species (e.g., water vapor) in the presence of corrosive gas (e.g., hydrogen chloride) by selecting the appropriate spectral window within which to measure absorption. In particular, a spectral region must be determined wherein (i) the contaminant or gaseous species has at least one absorption feature and (ii) the corrosive gas has essentially no interfering absorption features. By interfering absorption features is meant absorption features which overlap the absorption feature used to identify the gaseous species thereby causing the detection selectivity between the gaseous species and the corrosive gas to be compromised. Many such spectral windows (where the corrosive gas has no absorption or very weak absorption) exist within the absorption regions of a gaseous species. Since absorption by the corrosive gas is extremely weak (if measurable) within these spectral windows, ILS sensors 100 operating at these wavelengths can be used to detect the gaseous species without interference. Finding a wavelength region where such a spectral window exists, in order to avoid interfering spectroscopic signal, may require significant efforts. In particular, the enhanced detection sensitivity of ILS detection for measuring absorption in gases means that even interferences from background gases having weak absorption and/or extremely small absorber concentrations may be significant; even if such interferences are negligible with conventional spectroscopy techniques. Additionally, operation of an ILS laser 500 in a specific spectral region where a particular spectral signature exist may also require considerable effort.

Nevertheless, unique spectroscopic identification of a specific gas species can be routinely expected. Thus, selectivity in the gaseous species detected can be achieved. The existence of these spectral windows, however, may be evident only at high spectral resolution. Consequently, sufficient spectral resolution may be required to separate absorption features that appear near each other.

It will be further appreciated that the wavelength position and width of a specific spectral window depends directly on the specific gaseous species and the specific corrosive gas. For example, for detection of water vapor in hydrogen chloride (HCl), a spectral region may be selected from the wavelength region between about 1420 and 1434 nanometers (nm). Alternatively, a spectral region may be selected from the wavelength region between about 1433 and 1440 nanometers.

Accordingly, the ILS laser 500 must output light having a wavelength distribution at least a portion of which is in the selected spectral region.

In order to drive ILS laser 500, gas detection system 10 requires a pumping source which delivers radiation of sufficient power and within a suitable wavelength region so as to optically excite the ILS laser at or slightly above its threshold. In this regard, it is important that ILS laser 500 operate such that the gain in the laser medium exceeds the overall optical losses, including those associated with the gain medium, mirrors, and non-mirror intracavity optical elements, as well as the absorption of any gaseous species within the optical resonator cavity. Moreover, preferably laser 500 operates with multiple longitudinal modes, i.e., over a broad wavelength region. Typically, a desirable bandwidth over which laser action occurs is between about 2 nm and about 15 nm. While ILS laser 500 can also operate with more than one transverse resonator mode, such is not necessary. In accordance with a preferred exemplary embodiment of the present invention, the laser driver comprises an optical pumping laser 100. Suitably, the optical parameters (e.g., average power density, peak power density, divergence and beam diameter) of pumping laser 100 advantageously match the optical requirements of ILS laser 500. As will be appreciated, to do so it is necessary to determine how many photons can be delivered within a specific volume and at a given distance from the pumping laser 100 over a particular period of time. In general, in accordance with the present invention, such determinations are made in accordance with known theoretical and quantitative equations such that the pumping laser 100 is suitably selected to advantageously match the optical characteristics of ILS laser 500.

While other drivers may be utilized in the context of the present invention, preferably, a pumping laser 100 is selected on the basis of its operational wavelength and on its optical parameters in a manner such that it can alone be used to excite ILS laser 500. As will be described in greater detail hereinbelow, in cases where pumping laser 100 is not effective alone to drive (e.g., pump) ILS laser 500, beam modification optics, such as beam shaping assembly 200, can be utilized. Examples of beam modification optics include diffractive optics, refractive optics, gradient index optics wherein the refractive index varies axially, gradient index optics wherein the refractive index varies radially, micro-optics, and combinations thereof. However, in those cases where the radiation emanating from laser 100 suitably matches the pumping requirements (e.g., mode volume) of the ILS gain medium contained within ILS laser 500, such beam modification optics are unnecessary.

In accordance with one exemplary embodiment of the present invention, pumping laser 100 comprises a laser operating at a wavelength, $\lambda_p$, (which is this case is a solid state crystal laser, i.e., a Nd:YAG, operating at approximately 1064 nm having an output power greater than about 2.8 watts with a $TEM_{00}$ transverse mode structure). Suitably, a beam E propagating from pumping laser 100 has a linear polarization and is rotatable perpendicular to the plane of propagation. Preferably, the divergence of the output beam (beam E) from pumping laser 100 is on the order of less than 0.5 mrad and evidences a beam diameter on the order of less than 5 mm. A particularly preferred pumping laser 100 is model T20-1054C from Spectra Physics of Mountain View, Calif. As will be explained more fully hereinbelow, use of such a pump laser 100 typically requires use of beam shaping optics assembly 200.

It should be appreciated that driver 100 may comprise any suitable optical pumping source, either coherent or incoherent, continuous or pulsed, that will suitably excite ILS laser 500. As a result, even in accordance with the previously recited preferred embodiment, pumping source 100 operates in a conventional manner and emits radiation over a desired frequency band and having a desired bandwidth.

For example, pumping laser 100 may comprise a diode laser, see e.g., above-mentioned patent application Ser. No. 08/675,605 by G. H. Atkinson et al, entitled "Diode Laser-pumped Laser System for Ultra-sensitive Gas Detection Via Intracavity Laser Spectroscopy (ILS)". Use of a diode laser as a pump laser 100, however, typically requires use of a beam shaping optics assembly 200.

With continued reference to FIG. 2, ILS laser 500, in the simplest case comprises an optical resonator cavity defined by the entire optical path length between respective mirrors 501, 503, 505.

For gas samples containing corrosive gases, i.e., gases which chemically react with one or more of the laser components, it is desirable to separate the gas sample region from such components (e.g., gain medium, mirrors, etc.). In accordance with a preferred embodiment of the present invention, a separate sample system 400A may be advantageously utilized to isolate the sample from the laser components.

Figure 4:
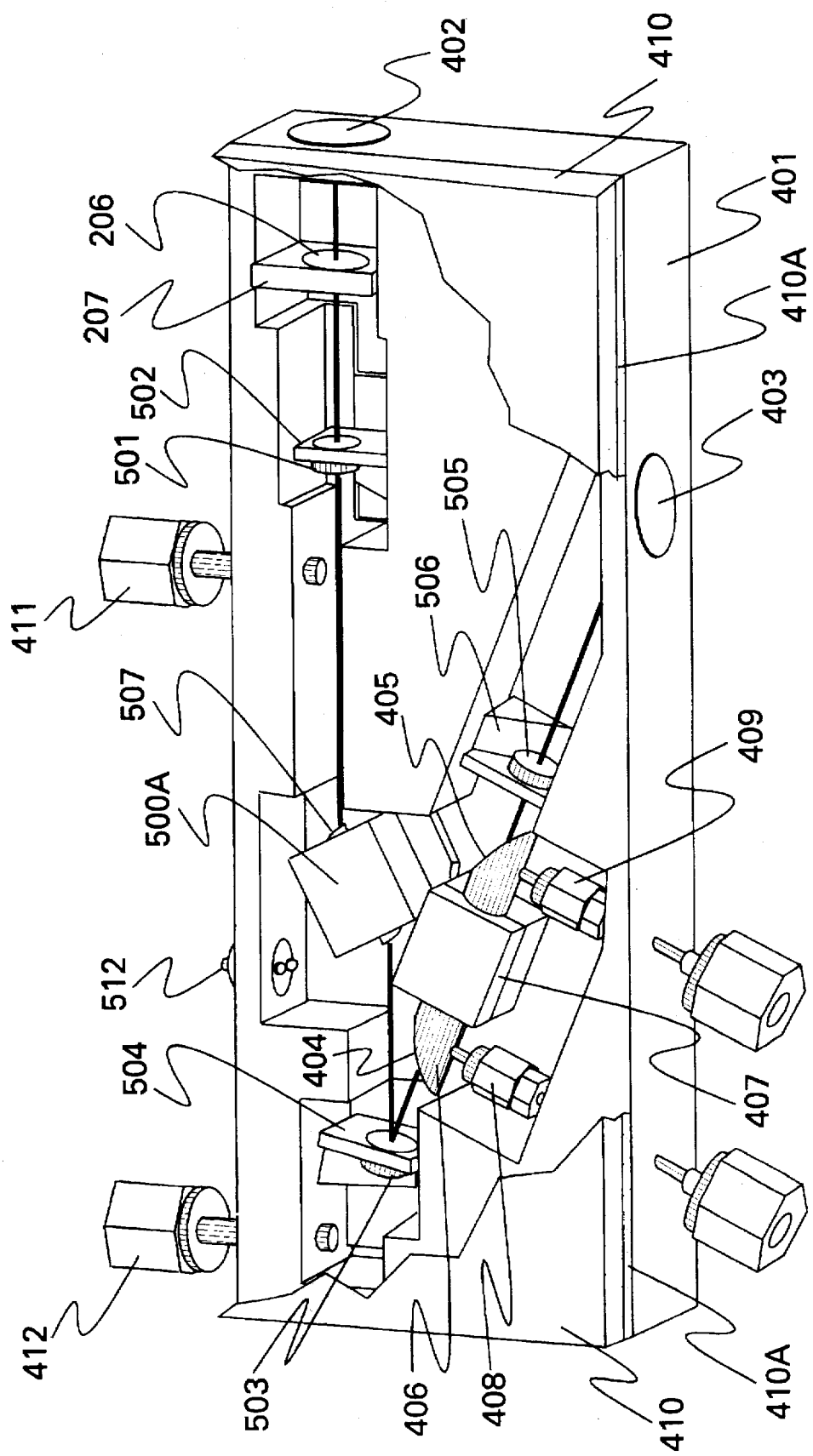
FIG. 4 is a schematic perspective view of an ILS chamber including the chamber components depicted in FIG. 2, some of the components shown in partially broken away fashion.

With reference to FIGS. 2 and 4, in accordance with this preferred aspect of the present invention, sample system 400A preferably comprises a gas sample cell body 406 suitably maintained within a gas sample cell holder 407. Respective cell windows 404 and 405 are suitably mounted on the distal ends of gas sample cell body 406 and provide optical access to the sample within the cell body. Windows 404 and 405 also suitably seal cell body 406. As will be discussed in greater detail below, the region in which system 400A is suitably placed is astigmatically compensated. Given this astigmatic compensation, windows 404 and 405 are not "active" optical elements which significantly alter or perturb the output the ILS laser beam except with respect to transmission. An inlet conduit 408 and an outlet conduit 409 are operatively connected to gas cell body 406.

With reference to FIG. 4, couplings 408 and 409 are advantageously employed to ensure efficient and effective passage of a gas sample into and out of gas (contaminant) sample cell system 400A. Accordingly, the gas detection system 10 of the present invention can continuously monitor a flowing gas at variable pressures including high pressure. In particular, the use of the gas sample cell body 406 advantageously enables the operation of the ILS laser 500 when measuring gases having a pressure which is different (i.e., higher or lower) than atmospheric pressure or the pressure for which the ILS laser was designed to lase. Without such a gas sample cell body 406, lasing would be difficult to achieve when monitoring a gas sample having a different pressure from the pressure at which the ILS laser 500 was aligned. Thus, the gas sample cell body 406 allows stable operation of the ILS laser 500 for a gas sample having a pressure in excess of atmospheric pressure or the pressure which the ILS laser was design to lase. Alternatively, the gas sample may have a pressure less than atmospheric pressure or the pressure which the ILS laser 500 was design to lase (e.g., when a vacuum exists in the gas sample cell body 406). Additionally, the gas sample cell body 406 enables stable operation of the ILS laser 500 for a gas sample having a pressure which fluctuates.

Suitably, cell body 406 comprises a stainless steel body having dimensions suitably in the range of 10 to 90 millimeters (mm). In accordance with a particularly preferred aspect of the present invention, sample system 400A defines an opening (i.e., the opening in body 406) having a diameter on the order of about one-eighth of an inch. Preferably, the opening in body 406 is symmetrically in the center of gas sample cell body 406. Preferably, the diameter of the opening in cell body 406 is suitably selected to be significantly larger than the diameter of the incoming beam such that optical alignment of gas sample system 400A may be easily obtained.

The thickness of windows 404, 405 is suitably selected to avoid interferometric effects which may interfere with the quality of the ILS absorption spectrum obtained through operation of the gas detection system 10. In accordance with this aspect, the material used in forming windows 404, 405 is optimally chosen to minimize absorption losses in the region over which ILS laser 500 operates, such as in the range of 1350 to 1550 nanometers (nm). For example, windows 404, 405 may be formed from an optically compatible material, such as Infrasil™, that is highly polished.

Windows 404, 405 are suitably oriented at Brewster's angle so as to further minimize reflective losses from the window surfaces.

As so configured, gas sample cell 406 suitably permits beam H to pass through the gaseous sample to be analyzed. Couplers 408, 409 with attached tubing are suitably selected to provide easy adjustment such as may be required to realign and/or align windows 404, 405 within ILS laser 500 without significantly altering the threshold pumping conditions. The resonator cavity, in the case where system 400A is employed, is suitably defined by the physical length between mirrors 501, 503, 505 (including the laser crystal 507 and including the region between windows 404, 405 as well as windows 404 and 405 themselves that comprise the sample system 400A).

It will be appreciated that it is necessary that any gases (contaminants) within chamber 400 that are to be detected are suitably removed or eliminated such that the absorption spectrum of the sample obtained through use of the gas detection system 10 is accurate as to the amount or presence of those gases (contaminants) within the gas sample contained within system 400A. In accordance with a preferred aspect of the present invention, chamber 400 advantageously evidences a sealed container which can be either purged of gas(es) (contaminant(s)) to be detected, or evacuated to remove gas(es) (contaminant(s)) to be detected, or in which the level of gas(es) (contaminant(s)) can otherwise be reduced below the level to be detected in the sample system 400A. Continuous removal of the contaminants can be achieved for example, by gettering, as described more fully below.

Referring to FIGS. 2 and 4, in accordance with a preferred embodiment of the present invention, ILS chamber 400 (excluding the sample system 400A) suitably comprises a container base 401 and attachable top 410. Respective windows 402, 403 are suitably positioned in the walls of body 401 in a suitable manner and position relative to the optical resonator cavity defined therewithin. Container base 401 and top 410 suitably comprise stainless steel or aluminum. Top 410 is advantageously secured to body 401 in accordance with any conventional technique suitable to permit evacuation, purging and/or further removal of contaminants therewithin. For example, a gasket 410A or other suitable means together with sealing devices (e.g., mechanical assists, metal seals, adhesives, and the like all not shown) may be employed for such purposes. Desirably, base 401 and top 410 are effectively sealed prior to delivery to a user in a relatively tamper-proof manner.

For the purpose of purging or evacuating chamber 400, an inlet 411 for vacuum pumping and/or purging as well as an outlet 412 for vacuum pumping and/or purging are provided.

Windows 402, 403 are suitably disposed in the walls of container 401, thereby providing optical access to ILS chamber 400. Preferably, window 402 is suitably provided with an antireflective (AR) coating on the order of about 1000 to 1100 nm, and optimally about 1064 nm. On the other hand, window 403 preferably comprises an optical window without an AR coating. Window 402 is suitably designed to provide for maximum transmission at the wavelength $\lambda_p$, in this case, 1064 nm. Similarly, window 403 is suitably designed to provide maximum transmission over the operational wavelength region of the ILS laser 500 (e.g., 1350 nm to about 1550 nm).

More particularly, reducing gases (contaminants) in chamber 400 (excluding sample system 400A) to an acceptable level may suitably comprise purging or evacuating sealable container 401 with top 410 such that the level of gases (contaminants) is below that to be detected in the gas sample within the sample system. It will be appreciated that the loss contributed by the gases in the chamber 400 will be comparable to loss contributed by the gases in the gas sample cell body 406 when the ratio between (1) the concentration of gases in the chamber and (2) the concentration of gases in the gas sample cell body is equal to the ratio between (1) the length of the cavity (i.e., between mirror 501 and mirror 505) and (2) the length that the ILS laser beam traverses in the cell body.

In such cases where the contaminant comprises water vapor, it is necessary that water levels in chamber 400 be reduced below those which are contained within the sample. In accordance with the present invention, detection levels of less than 1 part per billion (ppb) are obtainable in corrosive gas. While any now known or hereafter devised method for removing contaminants (e.g., water) from chamber 400 (excluding the sample system 400A) can be practiced within the context of the present invention, preferably, chamber 400 is appropriately sealed and inert gases, such as nitrogen are pumped therein. In some instances, it may be necessary to further evacuate the chamber 400 so as to create a vacuum which removes substantially all contaminants contained therein. Also, it may be useful to heat the chamber 400 while evacuating. Application of such heating or "baking" will enable a higher level of vacuum to be achieved if the chamber 400 is subsequently cooled while continually being evacuated. In accordance with yet a further aspect of the present invention, a getter (not shown) may be advantageously employed with chamber 400 to provide even further elimination of water within the chamber. As will be appreciated by those skilled in the art, a getter (e.g., a molecular sponge) having the capacity for continuously absorbing water may be utilized to reduce the level of water (contaminants) below the water concentration that is to be detected in the gas sample cell 406 (e.g., less than 1 ppb).

The gas sample is suitably communicated to system 400A by connecting a gas line to connectors 408, 409 and feeding the gas into sample system 400A.

As briefly mentioned above, ILS sensor 500 suitably optically detects gaseous species (contaminants, e.g., water vapor) contained in a gas sample placed within chamber 400. In accordance with the present invention, ILS laser 500 suitably comprises a crystal (gain medium) 507 mounted in a crystal holder 508. Crystal 507 is suitably mounted in crystal holder 508 such that crystal 507 also is optimally placed with reference to the incoming beam. As previously mentioned, the incoming beam is suitably shaped either by operation of pump 100 or through use of beam shaping assembly 200 such that incoming beam F suitably matches the mode volume of the ILS gain medium (e.g., crystal 507).

In general, ILS laser 500 is suitably configured such that the laser beam in the intracavity region is substantially parallel (i.e., astigmatically compensated) in the region where the beam is directed to the gas sample, e.g., as contained within system 400A. While a variety of optical configurations may be employed for this purpose, these mirror configurations have been found to be particularly advantageous. Such a configuration permits the accurate astigmatic compensation of the ILS laser beam thus permitting simultaneous meeting of the optical conditions necessary to pump ILS laser 500 at the lasing threshold and generation of a laser beam which is substantially parallel as it is directed to the gas sample, such as contained within system 400A.

In accordance with this aspect of the present invention, respective mirrors 501, 505 and a folding mirror 503 are suitably employed for this purpose. Mirror 501 preferably comprises an optical mirror having an AR coating optimally centered about $\lambda_p$, e.g., between about 1000 and 1100 nm, optimally 1064 nm. Mirror 501 also has a coating that effectively provides on the order of about 99.8% to about 100% reflectivity in the desired spectral region of operation of the ILS laser 500 (e.g., about 1350 to about 1550 nm). Suitably, mirror 501 comprises a concave mirror. For example, mirror 501 may have a radius of curvature (ROC) of about 10 centimeters (cm) and a diameter on the order of about 1.0 to about 1.30 cm. Preferably, mirror 503 comprises a folding mirror which is configured similarly to mirror 501 and has a similar reflection coating. In accordance with a preferred aspect of the present invention, mirror 503 has a coating suitable to achieve reflectivity of about 99.8% to about 100% over the desired spectral region (e.g., about 1350 to 1550 nm).

Preferably, mirror 505 comprises a flat mirror (ROC≈∞). With reference to FIG. 2, one side of mirror 505, the side facing mirror 503 is advantageously provided with a reflective coating in the desired spectral region for lasing of the ILS laser 500, e.g., between 1350 and about 1550 nm. The other side 505B of mirror 505 is suitably uncoated.

Preferably surfaces of mirror 505 are suitably wedged one against the other at an angle on the order of about 0.5 to about 3.0 degrees, optimally about 1.0 degree. The present inventors have found that wedging such surfaces in this manner tend to minimize undesirable reflections which may lead to interference effects.

Mounts 502, 504, and 506 enable mechanical adjustment to optically align the ILS cavity within chamber 400. For example, the present inventors have found that the efficiency of the ILS laser 500 is optimized for a laser configuration in which mirrors 501 and 505 are aligned for a beam incident angle of about 0° and mirror 503 is aligned for a beam incident angle of about 12.5°.

Through the appropriate design, placement, and configuration of mirrors 501, 503, and 505 beam H is substantially parallel (i.e., collimated) in the region between mirrors 503 and 505. As a result, sample system 400A can be inserted within the intracavity region without significant deleterious effects in the performance of ILS laser 500. It will be appreciated, however, that the distance between any reflective surfaces (e.g., mirrors and windows) within the ILS laser 500 must not be such that any interference occurs inside the ILS laser. Interference patterns are produced if the distance between the reflective surfaces equals an integer number of wavelengths comparable to the wavelength at which the ILS laser crystal 507 operates.

As described above, ILS laser crystal 507 preferably operates in a wavelength region suitable for detection of the contaminants contained within the gas sample (e.g., water vapor) over which a signature absorption spectrum can be obtained. As previously mentioned, laser crystal 507 generally exhibits the properties of a multimode laser system. It will be appreciated that the mode spacing of output of the laser crystal 507 is required to be small enough to accurately represent the absorption features of the gas sample. Light produced by laser crystal 507 typically has a mode spacing of about 450 megahertz (MHz) to about 550 MHz, preferably about 500 MHz, thus ensuring accurate spectral replication of absorption bands. While any crystal may be utilized in the context of the present invention, a $Cr^{4+}$:YAG or $Cr^{+4}$:lutetium (Lu)AG laser crystal may be optimally used in connection with the present invention for the detection of water vapor in HCl. Moreover, other hosts for the $Cr^{+4}$ ions may be used and other doped ions into these host crystals may be substituted. The present inventors have found that the low gain efficiency of a $Cr^{4+}$ system in a garnet host (e.g., YAG or LuAG) can be operated successfully as a laser using a crystal that is on the order of about 10 to 30 mm in length and 5 mm in diameter. Preferably, the doped concentration is in the range of about 0.10% to 0.30% in such garnet host. A particularly preferred laser gain medium 507 comprises a $Cr^{4+}$:YAG or $Cr^{4+}$:LuAG crystal cut at Brewster's angle to minimize reflective losses. More particularly, a $Cr^{4+}$:YAG crystal cut at Brewster's angle (e.g., for a crystal refractive index where n is about 1.82 and $\theta_B$ is about 61.20) having a crystal length of about 23 to 27 mm at about a 0.15% dopant level has been found to be particularly advantageous in the context of gas detection system 10 in accordance with the present invention. (Examples of other laser crystals that can be suitably employed in the present invention include aluminum oxide doped with titanium ions, $Ti^{3+}:Al_2O_3$, barium lithium fluoride doped with nickel ions, $Ni^{2+}$:$BaLiF_3$. A laser crystal comprising $Ti^{3+}:Al_2O_3$ outputs light having a wavelength between 0.680 to 1.100 micrometers when pumped with light having a wavelength of 0.500 micrometers. A laser crystal comprising $Ni^{2+}$:$BaLiF_3$ outputs light having a wavelength between 1.3 to 1.6 micrometers when pumped with light having a wavelength of 0.680 micrometers).

Laser crystals 507 currently available, while improving in efficiency, have considerable losses associated with them. The losses translate to heat. In accordance with the present invention crystal 507 suitably is mounted in a manner allowing for the effective removal of the heat thus generated in operation. It should be appreciated, however, that as the efficiency of laser crystals 507 continue to improve as new crystals are developed, the need or requirements on heat removing devices will be reduced and likely, at some point, the losses will be small enough that the need to remove the heat may be eliminated all together. However, using crystals 507 presently available, ILS laser system 500 preferably further comprises a heat sink system 500A.

Figure 5:
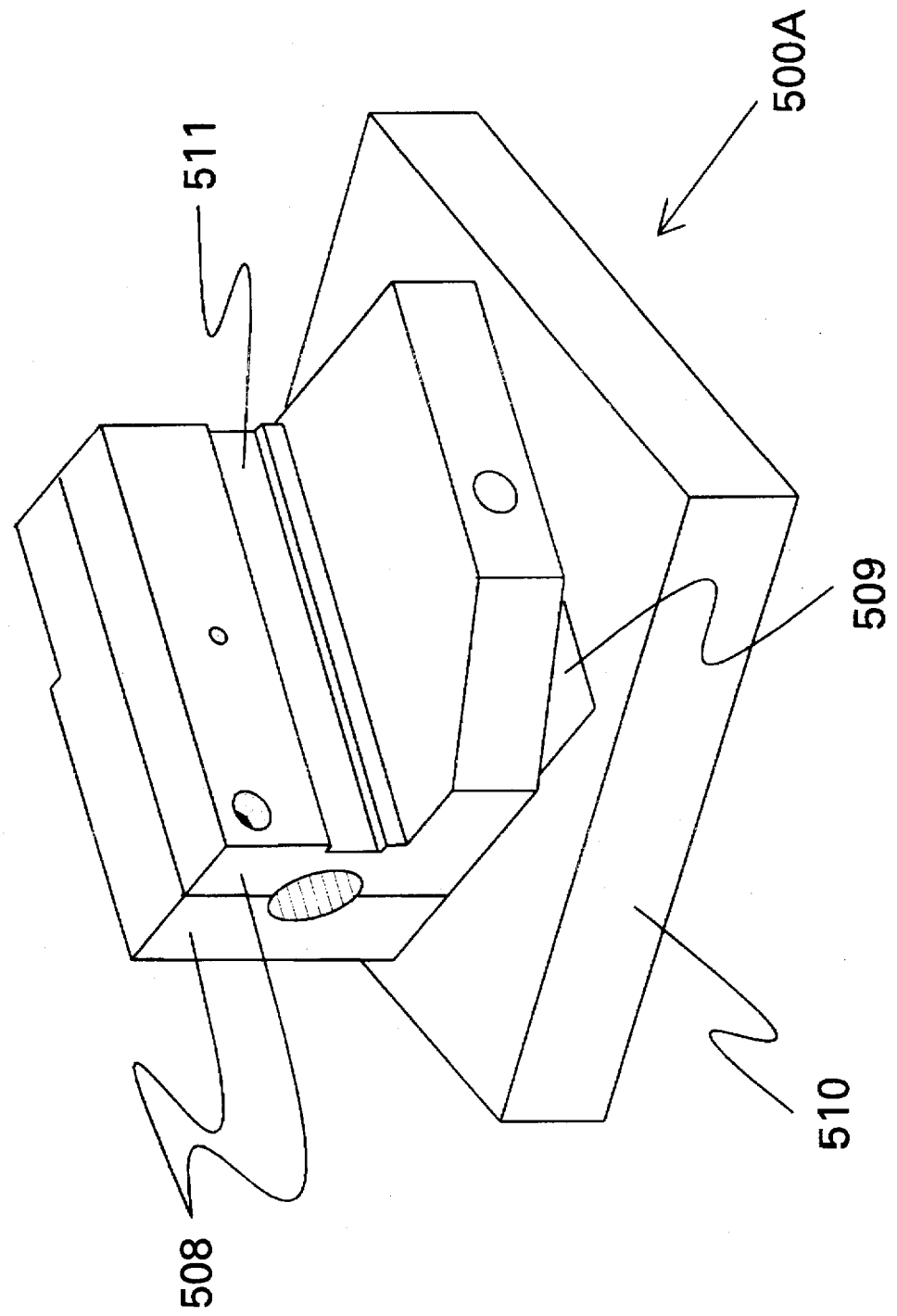
FIG. 5 is a perspective view of an exemplary ILS laser crystal holder and heat sink useful in connection with the contaminant detector system shown in FIG. 2.

With continued reference to FIG. 2 and additional reference to FIG. 5, heat sink system 500A is connected to mount 508 and crystal 507 (not shown in FIG. 5). As shown best in FIG. 5, holder 508 preferably comprises a two-part holder suitably arranged to mechanically hold the laser crystal 507. Heat sink system 500A preferably includes a copper heat sink bridge 510, a thermal electric cooler 509, and a thermal electric sensor 511. Additionally, an electrical temperature control interface 512 is provided in the walls of the body 401 of the chamber 400 (see FIG. 4). Mount 508 together with bridge 510, cooler 509, and sensor 511 serve to properly align crystal 507 with respect to the other optical elements comprising ILS laser 500, as well as enable control of the thermal properties of the crystal.

In accordance with the preferred aspect of the present invention, heat sink system 500A is in direct physical contact with crystal 507. Heat produced by normal operation of crystal 507 through optical excitation occasioned by beam F is effectively conducted away from crystal 507 thereby maintaining a relatively constant operating crystal temperature. Preferably, crystal holder 508 comprises copper/ aluminum which is operatively connected to cooler 509 and heat sink bridge 510. Suitably, heat sink 510 comprises a copper heat sink located in body 401 of chamber 400 such that excess heat is conducted away from crystal 507. Sensor 511 measures the temperature of holder 508, cooler 509, bridge 510, and crystal 507 such that optimum operating temperatures are maintained. In accordance with this aspect of the present invention, thermal management of crystal 507 is obtained, thereby eliminating the need for coolant liquids which may unnecessarily compromise and complicate the operation of the gas detection system 10.

ILS laser system 500 is suitably arranged such that the angle ($\phi$) of the beam exciting crystal 507 and the reflected beam from mirror 503 is on the order of about 20° to 30°, more preferably from about 23° to 27°, and optimally about 25°. This beam (beam H) is directed to the sample system 400A.

Output beam G from ILS laser 500 after passing through sample system 400A is directed to spectrometer assembly 600. Such direction can be obtained, such as shown in FIG. 2, through use of a folding mirror 601 suitably mounted in a mirror mount 602. Mirror 601 preferably comprises a plane mirror containing a coating for high reflectivity in the desired spectral region of operation of the ILS laser 500 (e.g., 1350 to 1550 nm).

It will be appreciated that the output from the ILS laser 500 can alternatively be transmitted via an optical fiber link to a remote site for spectral analysis. In particular, beam G can be coupled into an optical fiber or an optical fiber bundle. The output of the ILS laser 500, after having passed through the gaseous species, is thereby carried to the spectrometer assembly 600 which is located at the remote site. Under the proper conditions, it has been demonstrated that such optical fiber transmission does not distort the spectral data.

With continued reference to FIG. 2, spectrometer assembly 600 comprises dispersive gratings designed to spectrally resolve a coherent beam, in particular, the absorption spectrum of the contaminant in the sample to be detected. Suitably, the spectral dispersion of the spectrometer 600 is sufficiently large to clearly resolve the absorption features of such contaminant, thus enabling the identification of the "signature" of each contaminant and the quantitative determination of the concentration of the contaminant. While any now known or hereafter devised spectrometer may be utilized in accordance with the present invention, preferably spectrometer 600 comprises two diffraction grating assemblies 600A and 600B operating in conjunction with an optical beam expanding assembly 600C and a focusing lens assembly 600D. Optical beam expanding assembly 600C preferably comprises lenses 603 and 605 suitably mounted within the gas detection system 10 through use of mounts 604 and 606. Lens 603 preferably comprises a negative lens and lens 605 preferably comprises a collimating lens; each preferably having an AR coating centered about the absorption spectrum of the contaminant in the sample to be detected, e.g., between about 1000 nm and 1500 nm, optimally 1400 nm.

Diffraction grating assemblies 600A and 600B suitably comprise respective diffraction gratings 607 and 609 mounted on respective diffraction grating mounts 608 and 610. As will be appreciated, mounts 608, 610 permit tuning and adjustment of diffraction gratings 607, 609 within spectrometer assembly 600.

Focusing lens assembly 600D preferably comprises a lens 611 containing an AR coating at the wavelength at which the ILS laser 500 operates, e.g., between about 1000 nm and 1500 nm, optimally 1400 nm. The lens 611 focuses the output of the spectrometer 600 onto multichannel array detector 701.

The spectral region over which the ILS laser 500 operates is produced by spectrometer assembly 600 and is displaced spatially across a plane where the multichannel array detector 701 is suitably fixed on a mount 702. An electronic board 703 containing the control and timing electronics required to operate and read information from the multichannel detector 701 is operatively connected thereto. As a result, the entire spectrally dispersed absorption spectrum of the particular contaminant sought to be identified through use of the gas detection system 10 can be obtained. The positions and relative intensities of the specific absorption features of the contaminant can be utilized to uniquely identify the detected gas (contaminant) as well as quantitatively determine the amount of the gas (contaminant) so detected.

The detector 701 may comprise, for example, an InGaAs multichannel array detector with 256 pixels having 100 µm spacing. The light detected by multichannel detector 701 is preferably transduced into electronic signals at each detector element (pixel) with signals thereafter transferred to an analog-to-digital (A/D) converter 801 through board 703. Converter 801 is suitably connected through a BNC connector and shielded cable 704 such that the accurate transfer of information is ensured. Once the data is so converted, it is sent to a computer 802 which may be suitably programmed to convert the electronic signals into spectral information i.e., spectral signatures identifying a particular gas (contaminant) and concentration of gases (contaminants).

Alternatively, the output of the ILS laser 500 having passed through the gaseous species to be monitored can be directed to a spectrometer assembly 600 having at least one dispersive optical element (e.g., diffraction gratings 607 and 609) therein which can be scanned with respect to wavelength. The output of the spectrometer assembly 600 can then be directed to a single channel detector. The spectral signature of the gaseous species in the laser cavity is obtained by scanning the dispersive optical element while the light transmitted through the spectrometer assembly 600 passes through an appropriate aperture (e.g., slit) placed in front of the single channel detector. The intensity of the light transmitted through the spectrometer assembly 600, i.e., the output of the spectrometer assembly 600, is recorded as the dispersive optical element is scanned.

With reference now to FIG. 2, as previously mentioned, the gas detection system 10 detects the spectrally resolved region over which the ILS laser 500 operates once pumping laser 100 causes the ILS laser to operate at or near its threshold level. In cases where the optical characteristics of driver 100 suitably match those of ILS laser 500, no additional modification of the output of driver 100 is necessary. However, in those cases where the volume of the pumping radiation from driver 100 that is transferred to the gain medium (i.e., crystal 507) does not suitably match the volume that must be optically excited within the gain medium of ILS laser 500, beam modification system 200 can be utilized to facilitate such volume matching. In its simplest form, beam modification system 200 preferably comprises an optical telescope useful to optimize the radiation delivered to ILS laser 500 by focusing the required photon density into the correct location and volume of the gain medium of the ILS laser. Specifically, beam modification system 200 is used to alter the pumping radiation of driver 100 to meet the requirements of ILS laser 500.

In accordance with the present invention, beam modification system 200 may comprises a beam expanding telescope. Specifically, in such cases where pumping laser 100 comprises the preferred Spectra Physics diode pump solid state crystal laser and ILS crystal 507 comprises a $Cr^{4+}$:YAG or a $Cr^{4+}$:LuAG crystal, beam expansion of the pumping laser output maybe necessary.

Figure 6:
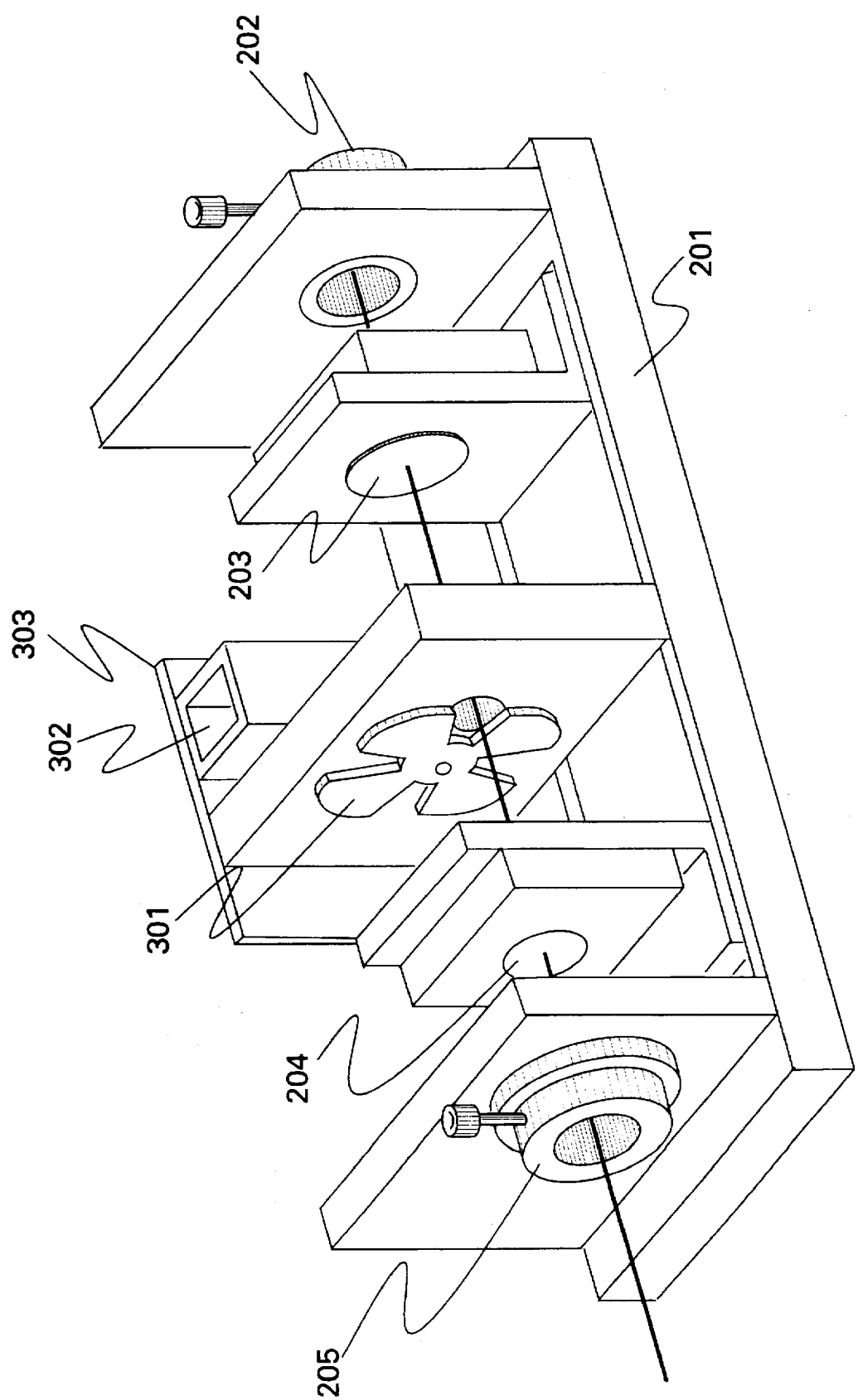
FIG. 6 is an enlarged perspective view of an exemplary embodiment of a beam shaping assembly including a chopper element which may be advantageously used in connection with the contaminant detector system shown in FIG. 2.

As shown best in FIG. 6, system 200 suitably comprises a series of lenses and adjustable apertures. In particular, a frame 201 is provided which suitably includes respective upstanding walls into which respective variable aperture devices 202 and 205 are suitably provided. While any appropriate means of varying the aperture of the opening into which the output (e.g., beam E) of laser 100 enters or exits system 200 may be employed, suitably, devices 202 and 205 comprise conventional aperture varying devices. System 200 also preferably includes a focusing lens 203 and a collimating lens 204. Preferably, lens 203 comprises a focusing lens and lens 204 preferably comprises a collimating lens both of which have an AR coating at the wavelength, $\lambda_p$, e.g., at about 1000 to 1100 nm, optimally about 1064 nm. As shown in FIG. 6, lenses 203 and 205 are suitably attached to frame 201 to permit their respective alignment within beam E.

With continued reference to FIG. 2, in some applications, it may be necessary that the incoming beam be appropriately focused into the laser gain medium (e.g., ion-doped crystal or glass) 507 within ILS laser 500. In accordance with the preferred aspect of the present invention, a focusing lens 206 may be advantageously mounted in a laser lens mount 207 such that the focusing lens is suitably located within the path of beam F. In accordance with a particularly preferred aspect of the present invention, focusing lens 206 suitably comprises an optical focusing lens with an AR coating centered about a wavelength $\lambda_p$, e.g., between about 1000 and 1100 nm and optimally 1064 nm coating. Focusing lens 206 may be suitably configured to evidence a plano-convex or convex-convex configuration.

As will be appreciated by those skilled in the art, the quality of the quantitative information obtainable through use of the gas detection system 10 depends, at least in part, on stable operation of ILS laser 500. In the context of the present invention, the stability of laser 500 depends directly on how reproducibly ILS laser 500 reaches threshold. Desirably, pumping laser 100 suitably pumps ILS laser 500 continuously near threshold where its greatest sensitivity may be obtained. However, not all drivers are capable of reliably operating in a continuous fashion. In addition, operating continuously tends to require substantial effort to maintain amplitude and wavelength stability of the ILS laser 500 which may have an adverse impact on cost and thereby produce an adverse impact on the commercial viability of the gas detection system 10.

As an alternative to operating ILS laser 500 continuously, and in accordance with a preferred embodiment of the present invention, the ILS laser is operated in a "pulsed mode" or a "chopped mode". As used herein, the terms "pulsed mode" and "chopped mode" refer to processes for reproducibly exposing ILS laser 500 (i.e., ion-doped crystal 507) to pumping radiation such that the ILS laser will be switched on and off. Chopping corresponds to causing the pump radiation to alternate between zero intensity and a fixed intensity value at a fixed frequency and over a fixed (often symmetric) duty cycle. In contrast, pulsing corresponds to causing the pump radiation to alternate between zero intensity and a non-zero intensity (which is not necessarily fixed) over a duty cycle which may be varied and which is typically asymmetric. (Alternatively, the pump radiation can be modulated such that the intensity of the pump beam does not reach zero intensity but fluctuates alternately between at least two intensity levels which brings the ILS laser 500 alternately above and below threshold).

Through operation in the chopped mode or the pulsed mode, stable operation of ILS laser 500 consistent with the quantitative spectral and concentration measurements may be obtained in a commercially viable manner. Such intensity modulation (e.g., interruption) can be achieved utilizing, among other things, a mechanically operated chopper, an acousto-optic modulator, a shutter, and the like.

Alternatively, the output intensity of pump laser 100 may be modulated instead of secondarily chopping the output beam (beam E). In particular, if the pump laser 100 comprises a diode laser, the electrical power supplied to the diode laser pump laser can be modulated to alternately obtain voltages just above and below that required to cause the ILS laser 500 to lase. Consequently, the ILS laser 500 will be turned on and off.

While any now known or hereafter devised manner of producing a chopped mode or a pulsed mode can be utilized in accordance with the present invention, advantageously such modes are obtained through use of modulation assembly 300.

In accordance with this aspect of the present invention, beam E is periodically prevented from reaching ILS laser 500 by a rotating modulator 301 which periodically blocks and transmits the pumping laser beam E. Specifically, in FIG. 6, modulator 301 comprises a mechanical chopper. Mechanical chopper 301 is suitably placed so that beam E is modulated before reaching ILS laser 500. While modulator 301 may be advantageously placed before or after beam modification system 200, in accordance with a preferred embodiment of the invention, the chopper is suitably placed at the focal point within beam modification system 200. Alternatively, the chopper 301 may be placed in front of the pump laser 100. As best illustrated in FIG. 2, chopper 301 is suitably mounted in frame 201 of the beam modification assembly 200.

It should be appreciated that chopper 301 could be replaced by any device, e.g., mechanical or electro-optical, which periodically blocks or modulates the pumping laser beam. As previously mentioned, in accordance with the present invention, the intensity of the pumping radiation emanating from pump laser 100 must only fall below that required to make ILS laser 500 reach threshold and therefore, is not required to reach a zero value. It will be further appreciated, however, that the total optical pumping energy (i.e., the integrated intensity) delivered by the pump laser 100 to the ILS laser 500, during each period of modulation, must remain constant.

With either the pulsed mode or chopped mode, the output of ILS laser 500 which contains the absorption information, may be periodically sampled. Referring again to FIG. 2, in accordance with a preferred embodiment of the present invention, modulation assembly 300 comprises modulator 301 (provided with appropriate electronic circuitry) and modulator 304 (also provided with appropriate electronic circuitry). Modulator 301 advantageously modulates the intensity of output beam E from pump laser 100 and lens 203, while modulation device 304 suitably modulates the output beam of ILS laser 500 that exits chamber 400, thereby periodically sampling the output of the ILS laser. Suitably, modulator 301 alternately blocks pumping beam E from reaching ILS laser 500 gain medium (e.g., crystal 507), while modulator 304 alternately blocks ILS laser beam exiting chamber 400 from reaching both spectrometer assembly 600 and detector assembly 700.

Suitably, chopper 301 rotates between an open and closed position. Chopper 301 is suitably driven by a chopper driver 303 connected to chopper through use of a suitable electrical connector(s) 302. As driver 303 causes chopper 301 to rotate to the open position, beam E reaches ILS laser 500, thereby bringing ILS laser 500 above threshold for laser activity. ILS laser 500 continues to operate until driver 303 causes chopper 301 to rotate to the closed position, whereupon chopper 301 effectively blocks pumping beam E from reaching ILS laser 500.

ILS laser 500 output exiting chamber 400 is suitably directed to modulator 304. In accordance with various aspects of the present invention, modulator 304 comprises an acousto-optic modulator. It should be appreciated, however that other available devices, for example, another mechanically operated chopper or even a shutter may be suitably employed for this purpose. As discussed above, to extract quantitative information from the ILS laser 500 exiting beam, modulator 304 periodically samples the output of the ILS laser which contains the absorption data of contaminants (e.g., gaseous species) contained in the particular sample. (It will be appreciated that instead of employing modulator 304, detector assembly 700 may be alternately switched on and off to periodically sample the output of ILS laser 500 as will be discussed more fully below).

While the specific form of modulation is variable, use of modulation enables generation of a reproducible, effective optical path length within ILS laser 500. Stated another way, by varying the generation time ($t_g$), i.e., the time period over which intracavity mode competition within ILS laser 500 is permitted to occur, the effective absorption path length within the intracavity resonator can be controlled and selected to achieve optimum quantitative application of the ILS gas detector 10.

Advantageously, modulation of the output of the pump laser 100 is advantageously synchronized with modulation device 304 such that quantitative information from ILS laser 500 can be extracted in a time-resolved manner. Pump radiation E is effectively delivered to ILS laser 500 intermittently by passing pump beam E through chopper 301. Delivering radiation intermittently alternately brings ILS laser 500 above threshold and below threshold. After the generation time $t_g$, i.e., elapses as ILS laser 500 reaches its threshold, the ILS laser output is deflected by modulator 304 to the entrance of spectrometer assembly 600 and detector assembly 700 for detection. However, ILS laser 500 output beam G is deflected to spectrometer assembly 600 and detector assembly 700 for only a short time interval determined by the synchronization of modulation devices 301 and 304. The synchronization of modulators 301 and 304 ensures that radiation from ILS laser 500 is sampled over a well-defined time interval ($t_g$).

Synchronization of modulators 301 and 304 may be achieved by several conventional methods such as, for example, through electronic control by a digital circuit (not shown) operated by computer 802 operatively connected to gas detection system 10. Typically, synchronization of modulators 301 and 304 will be suitable to generate generation times ($t_g$) on the order of less than about 300 to 500 microseconds (μsec), more preferably on the order of less than about 10 to 100 μsec, and optimally on the order of less than about 1 μsec. Such synchronization results in the modulation assembly 300 allowing the output of the pump laser 100 to pass uninterrupted when modulator 304 is closed. The time interval between when the output of the pump laser 100 is not interrupted by the modulation assembly 300 and when modulator 304 opens is determined by $t_g$.

The generation time, $t_g$, can be varied without the use of modulator 304 by pulsing the output of the pump laser 100. As described above, pulsing corresponds to causing the pump radiation to alternate between zero intensity and a non-zero intensity value over (which is not necessarily fixed) over a duty cycle which may be varied, thereby bringing the ILS laser 500 alternately below and above threshold. Accordingly, the ILS laser 500 is turned off and on. The duration over which the ILS laser 500 lases may be varied by changing the duty cycle of the output of pump laser 100; in particular, the duration over which the pump laser pumps the ILS laser to threshold. Accordingly, the generation time ($t_g$), i.e., the time period over which intracavity mode competition within ILS laser 500 is permitted to occur, is varied. In this case, the detector assembly 700 remains continuously activated and the output of the ILS laser beam exiting chamber 400 is allowed to continuously reach the spectrometer assembly 600 and the detector assembly.

As described above, however, the total optical pumping energy or integrated intensity delivered by the pump laser 100 to the ILS laser 500 during each period of modulation must remain constant, even though the duration over which the of the ILS laser outputs light is changed. To maintain a constant total optical pumping energy, the intensity level of the pump beam is adjusted with each different period of modulation over which $t_g$ is to be varied. Accordingly, both the intensity of the pump beam and duration over which the laser diode pump laser 100 pumps the ILS laser 500 to threshold, are a changed to provide different generation times.

Pulsing the output of the pump laser 100 can be achieved by eternally controlling the transmission of the pump beam with a "pulser". Alternatively, if the pump laser 100 is a diode laser, the output intensity of the diode laser pump laser may be modulated by varying the electrical power supplied to the diode laser. (As described above, the electrical power supplied to a diode laser pump laser 100 can be modulated to alternately obtain voltages just above and below that required to cause the ILS laser 500 to lase).

Accordingly, the gas detection system 10 of the present invention may include any of the following configurations each of which enables the generation time to be varied:

(1) The output of the pump laser 100 may be chopped with an external chopper (e.g., chopper 301) and the detector 700 may be continuously activated with transmission of the output from the ILS laser 500 to the detector being controlled by a pulser (e.g., modulator 304) to enable periodically sampling;

(2) The output of the pump laser 100 may be chopped with an external chopper (e.g., chopper 301) and the detector 700 may be pulsed on and off to enable periodical sampling of the output from the ILS laser 500;

(3) The output of the pump laser 100 may be pulsed with an external pulser and the detector 700 may be continuously activated with the duration of the interaction between the output of the ILS laser 500 and the gaseous species being controlled by the duration of the pulses from the pump laser which cause the ILS laser to lase;

(4) In the case where the pump laser 100 is a diode laser, the output of the diode laser may be pulsed by varying the electrical power supplied to the diode laser and the detector 700 may be continuously activated with the duration of the interaction between the output of the ILS laser 500 and the gaseous species being controlled by the duration of the pulses from the diode laser which cause the ILS laser to lase;

(5) In the case where the pump laser 100 is a diode laser, the output of the diode laser may be chopped by varying the electrical power supplied to the diode laser and the detector 700 may be continuously activated with the transmission of the output from the ILS laser 500 to the detector being controlled by a pulser (e.g., modulator 304) to enable periodical sampling; and (6) In the case where the pump laser 100 is a diode laser, the output of the diode laser may be chopped by varying the electrical power supplied to the diode laser and the detector 700 may be pulsed on and off to enable periodical sampling of the output from the ILS laser 500.

In the embodiment of the gas detection system 10 of the present invention described above, the ILS laser 500 has a laser cavity formed from three mirrors (i.e., mirrors 501, 503, and 505) wherein mirror 503 is a folding mirror. As described above, this configuration of three mirrors is designed to provide an astigmatically compensated or substantially parallel beam in the region between mirrors 503 and 505.

Alternatively, the gas detection system 10 of the present invention may comprise an ILS laser 500 having a simplified laser cavity. In such an alternative embodiment of the present invention, the laser cavity is not designed to provide astigmatic compensation. Rather, the laser cavity may be formed between two mirrors thereby having a substantially linear configuration which does not provide astigmatic compensation; see e.g., patent application Ser. No. 08/675,531, filed on even date herewith by G. H. Atkinson et al, entitled "Linear Cavity System for Ultra-sensitive Gas Detection Via Intracavity Laser Spectroscopy (ILS)". However, the linear cavity design employed by such an alternative embodiment of the present invention enables a gas detection system 10 to be constructed which is substantially smaller and simpler. Consequently, such an embodiment of the gas detection system 10 of the present invention is less expensive to construct as well as easier to operate than the embodiment described above. Additionally, this alternative embodiment of the present invention based on a linear laser cavity can be constructed to be more rugged or mechanically stable as is required by many practical applications.

By "linear laser cavity" is meant a laser cavity that is equivalent to a laser cavity formed between only two mirrors. In its simplest form, a linear laser cavity comprises a laser cavity formed between a first mirror and a second mirror. It will be appreciated that any number of additional mirrors which are planar may be included to steer (i.e., alter the path) of a beam which travels from the first mirror to the second mirror. The inclusion of these additional mirrors, however, does not modify the shape of the beam within the laser cavity (provided that the distance between the first mirror and the second mirror is not changed). Accordingly, the inclusion of additional planar mirrors in a laser cavity of a laser does not affect the operation of the laser but merely alters the manner in which the laser is physically configured. Consequently, a laser cavity formed between a first mirror and a second mirror, having additional planar mirrors therebetween, is equivalent to a laser cavity formed solely between the first mirror and the second mirror; removing the additional planar mirrors alters neither the shape of the beam nor the operation of the laser. The use of such additional planar mirrors, however, may be employed to fit a laser cavity into a package having spatial constraints.

Thus, there has been disclosed an apparatus for detecting the presence and concentration of contaminants in a gas sample containing a corrosive gas by utilizing gas detection system 10. In accordance with a preferred embodiment of the present invention, a method for high sensitivity detection is also disclosed herein. The method for detecting the presence of a gaseous species in a gas sample containing a corrosive gas requires that a spectral region be selected wherein (i) the gaseous species has at least one absorption feature and (ii) the corrosive gas has essentially no interfering absorption features. (As described above, an interfering absorption feature corresponds to an absorption feature which overlaps the absorption feature used for identifying the gaseous species, such that, detection selectivity between the gaseous species and the corrosive gas is compromised). In accordance with the method of the present invention, a laser comprising a laser cavity and a gain medium 507 which outputs light having a wavelength distribution at least a portion of which is in the selected spectral region, is provided. The ILS laser 500 is contained in a sample chamber 400. A gas sample cell 406 having windows 404 and 405 which are transparent to light in the selected spectral region, such that a beam of light can pass through the gas sample cell, is also provided. The gas sample cell 406 is inserted in the ILS laser 500 such that output light from the gain medium 507 passes through the gas sample prior to exiting the laser cavity. The gases (contaminants) in sample chamber 400 are reduced to an acceptable level. The sample of gas to be detected is placed in the gas sample cell 406. The ILS laser 500 is pumped at or near threshold and the optical output from ILS laser 500 is periodically sampled, preferably via modulation assembly 300. The absorption spectrum of the gases (contaminants) within the sample is measured with spectrometer 600 and detection assembly 700. The absorption spectrum is analyzed to identify the gaseous species (contaminants) and determine its concentration within the sample utilizing computer/software system 800.

More particularly, reducing gases (contaminants) in chamber 400 (excluding the gas sample cell 406) to an acceptable level may suitably comprise purging or evacuating sealable container 401 with top 410 such that the level of gases (contaminants) is below that to be detected in the gas sample within the gas sample cell 406. As discussed previously, other mechanisms for reducing the level of gases (contaminants) may be utilized provided they can reduce the level to an acceptable level. Preferably, container base 401 is sealed to top 410 and contaminants contained therein are effectively removed (or reduced to an acceptable level). Desirably, base 401 and top 410 are effectively sealed prior to delivery to a user in a relatively tamper-proof manner.

A sample is suitably communicated to gas sample cell 406 by connecting a gas line to connectors 408, 409 and feeding the gas into the gas sample cell (for example, when the sample comprises a corrosive or reactive gas).

Pumping ILS laser 500 at or near threshold, more particularly, comprises selecting the correct pump laser 100 power, focusing conditions at laser crystal 507 utilizing beam modification optics 200 and lens 206, and modulation conditions utilizing modulator system 300. The method for detecting gaseous species in accordance with the present invention further comprises driving ILS laser 500 at threshold or near to but above threshold. In accordance with the present invention, driver 100 suitably pumps ILS laser 500. Where necessary, pumping beam E is suitably shaped by beam shaping assembly 200 to meet the optical requirements of ILS laser 500. Further, where gas detection system 10 is operated in a pulsed or chopped mode, as described above, modulation assembly, and in particular, modulator 301 may periodically interrupt pump beam E thereby preventing beam E from reaching ILS laser 500. Beam F output from modulator 301 and beam shaping assembly 200 is suitably directed to ILS laser 500.

In accordance with this method, as beam F enters chamber 400 through window 402 disposed in the wall of sealed container body 401, beam F is suitably directed to ILS laser 500. Additional focusing and direction of beam F may suitably be achieved as beam F passes from window 402 to focusing lens 206, where focusing lens 206 suitably focuses beam F and directs it through mirror 501. Beam F suitably pumps crystal 507 at or near threshold, and the output beam is suitably directed to the gas sample within the gas sample cell 406, such as by mirrors 503 and 505. The exiting beam, containing the absorption data from the gas (contaminant) sample, then exits gas chamber 400 through window 403 suitably disposed in a wall of sealed container body 401.

ILS laser 500 may be operated in a pulsed mode or a chopped mode using modulator 304, suitably synchronized to modulator 301, and which periodically samples the output beam from the ILS laser and passes the sampled output thus obtained to spectrometer assembly 600 and detector assembly 700. Alternatively, in the case where the pump laser 100 comprises a diode laser, the electrical power supplied to the diode laser pump laser may be modulated and synchronized with modulator 304. Suitably, mirror 601 directs sampled output beam G from ILS laser 500 to spectrometer assembly 600 and detector assembly 700. Alternatively, instead of using modulator 304, detector assembly 700 may be switched on and off to sample the output from ILS laser 500.

The method for detecting gaseous species in accordance with the present invention further comprises analyzing the output beam G sampled from ILS laser 500. Preferably, spectrometer assembly 600 spectrally resolves and detector assembly 700 suitably analyzes beam G from sampled ILS laser 500. Spectrometer assembly 600 suitably spectrally disperses beam G from ILS laser 500 through beam expanding assembly 600C, diffraction assemblies 600A, 600B and focusing assembly 600D. Spectrally-resolved ILS absorption data exiting spectrometer assembly 600 is suitably displaced spatially to be detected by detector assembly 700 comprising e.g., multichannel detector 701.

Figure 7:
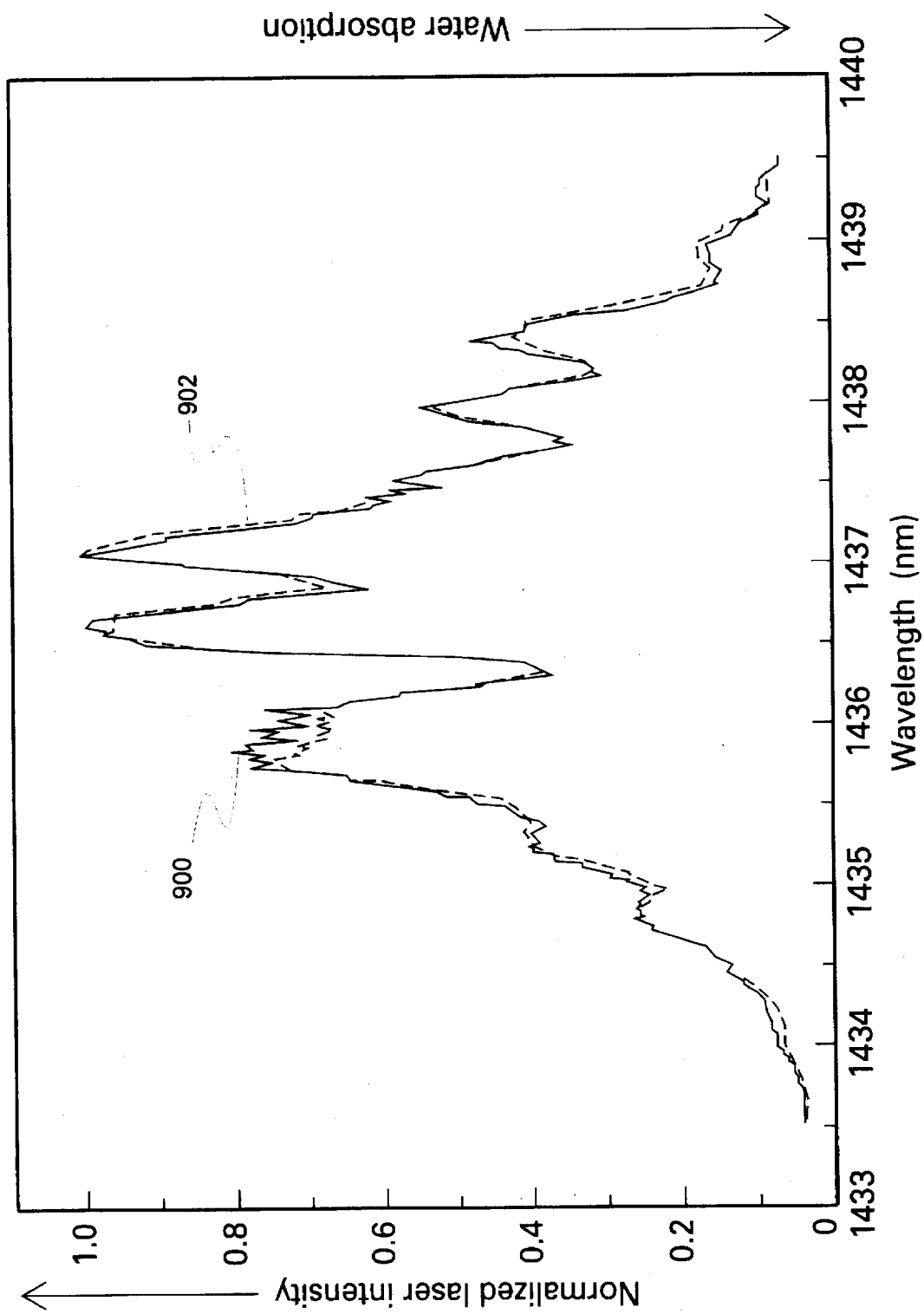
FIG. 7 depicts plots showing exemplary water absorption spectra in $N_2$ and HCl gases over the wavelengths of 1433–1440 nanometers.
Figure 8:
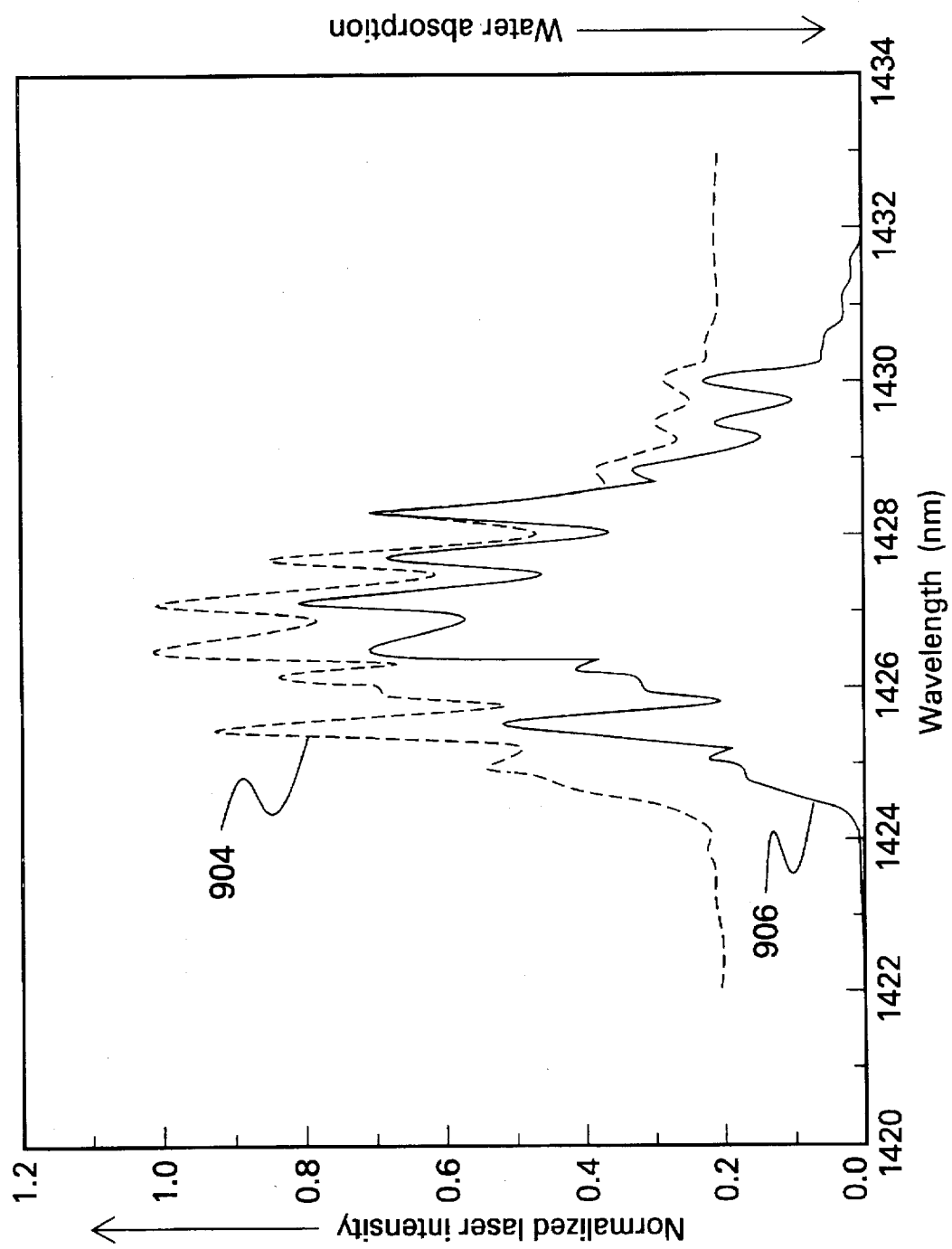
FIG. 8 depicts plots showing ILS water absorption in $N_2$ and HCl gases over the wavelengths of 1420–1434 nanometers.

It will be appreciated that the gas detection system 10 and method of the present invention can be utilized to obtain the absorption spectra for contaminants, such as water vapor, in a corrosive or reactive gas, such as HCl, or a non-corrosive gas, such as $N_2$, over a variety of wavelength regions. In particular, FIGS. 7 and 8 show that the signatures of a water vapor in each environment (corrosive or non-corrosive) can be obtained through operation of gas detection system 10. Specifically, FIG. 7 shows a plot of normalized laser intensity/absorption vs. wavelength for water in HCl (curve 900) and in $N_2$ (curve 902) over the region of about 1433 to 1440 nm while FIG. 8 shows a similar plot of normalized laser intensity/absorption vs. wavelength for water in HCl (curve 904) and in $N_2$ (curve 906) over the wavelength region of about 1420 to 1434 nm. The spectrum displayed in FIGS. 7 and 8 were obtained with the spectrometer assembly 600 and by measuring the output of diode 701. As will be appreciated, each data point illustrated results from a variety of measurements.

The data presented in the plots shown in FIGS. 7 and 8 demonstrate that water can be successfully detected in hydrogen chloride using the method of the present invention. Additionally, the observation that the water absorption spectra are the same, regardless of whether the measurement is made in hydrogen chloride or nitrogen, demonstrates that there are no spectral interferences from hydrogen chloride even though it is present at an extremely high concentration (e.g., one atmosphere total pressure).

Given the relationship between intensity and concentration, once a characteristic signature of the contaminant gas, e.g., water vapor, is obtained, the concentration of the contaminant contained within the sample can be readily obtained. In accordance with the present invention, computer 802 can be suitably programmed to interpret the data and provide an output indicative of the presence and/or concentration of the contaminant contained within the sample.

(It will be appreciated that the absorption feature(s) found in the spectral signature must be calibrated. Since intracavity laser spectroscopy offers increased sensitivity beyond prior art methods, weak transitions previously not measured may become measurable for the first time with the gas detection system 10 of the present invention. In such cases, these weak transitions can be used to identify the spectral signature and certify the presence of the gaseous species. Such weak transitions can also be calibrated by the gas detection system 10 thereby enabling the concentration of the gaseous species to be determined by the intensity of the absorption feature(s) corresponding to these weak transitions).

While the present invention is shown above as applied to obtaining the absorption spectra for contaminants, such as water vapor, in a corrosive gas, such as HCl, it will be apparent by those skilled in the art that other suitable contaminants and corrosive or reactive gases may also be employed in the practice of the present invention. Examples of corrosive gases suitably employed with the present invention include, but are not limited to, the following: $N_2O$, NO, $NO_2$, HONO, $HNO_2$, SO, $SO_3$, $H_2SO_4$, $Cl_2$, ClO, $Cl_2O_2$, HOCl, $PH_3$, OCS, HI, HF, HBr, $BCl_3$, $NF_3$, $BCl_2$, BCl, $SO_2$, $BF_3$, $Br_2$, $I_2$, $F_2$, $O_3$, $AsH_3$, $NH_3$, $SiH_4$, $B_2H_4$, $HNO_3$, HCN, HNC, $H_2S$, $COF_2$, and $CH_{4-x}X_x$, where X is F or Cl and x equals 1 to 4. It is not intended that the corrosive or reactive gases specifically disclosed herein, including those listed above, are to be exhaustive; rather, other corrosive or reactive gases may be employed as is suited to the particular use contemplated. For example, the corrosive gas may comprise other corrosive gases employed in the fabrication of semiconductor components. Additionally, it will be appreciated that the corrosive gas may comprise a combination of any number of corrosive gases such as those listed above. It will further be appreciated that the gaseous species to be detected may comprise, but is not limited to, one or more of the above listed corrosive gases.

Those skilled in the art will appreciate that the detection levels available through practice of the present invention generally exceed those which are obtainable through use of conventional devices. Moreover, gas detection system 10 can be used in-line and obtain ready, near real-time measurement of the presence and amount of the contaminant contained in a specific corrosive sample, thus addressing the many disadvantages associated with the use of such conventional devices. In particular, the method of the present invention provides rapid, in situ water vapor detection within gas samples containing corrosive gases at detection levels which are not available in prior art.

It should be understood that the foregoing description relates to preferred exemplary embodiments of the invention, and that the invention is not limited to the specific forms shown herein. Various modifications may be made in the design and arrangement of the elements set forth herein without departing from the scope of the invention as expressed in the appended claims. Moreover, the application of gas detection system 10 as well as the location of the ILS gas detector, e.g., in a semiconductor fabrication assembly, can vary as may be desired. For example, the specific placement of the various elements within the ILS chamber 400 and the gas detection system 10 itself may be modified so long as their configuration and placement suitably enables optical excitation of ILS laser 500 in a readily reproducible manner. These and other modifications in the design, arrangement, and application of the present invention as now known or hereafter devised by those skilled in the art are contemplated by the amended claims.

What is claimed is:

1. A method for detecting the presence of gaseous species in a gas sample containing corrosive gas, comprising the steps of:
    (a) selecting a spectral region wherein (i) said gaseous species has at least one absorption feature and (ii) said corrosive gas has essentially no interfering absorption features;
    (b) providing a laser comprising a laser cavity and a gain medium which resides therein, said gain medium outputting light having a wavelength distribution at least a portion of which is in said selected spectral region;
    (c) providing a gas sample cell having windows which are transparent to light in said selected spectral region such that a beam of light can pass through said gas sample cell;
    (d) inserting said gas sample cell in said laser such that light output from said gain medium passes through said gas sample cell prior to exiting said laser cavity;
    (e) inserting said gas sample containing said corrosive gas in said gas sample cell such that light output from said gain medium passes through said gas sample, said gas sample sealed within said gas sample cell such that said corrosive gas does not react with said laser; and
    (f) directing said light output from said gain medium after exiting said laser cavity to a detector assembly for determining the presence and/or concentration of said gaseous species in said gas sample.

2. The method of claim 1 wherein said gain medium comprises an ion-doped crystal.

3. The method of claim 2 wherein said gain medium is pumped by a pump laser selected from the group consisting of a solid state crystal laser and a diode laser.

4. The method of claim 1 wherein said corrosive gas comprises a gas selected from the group consisting of HCl, $N_2O$, NO, $NO_2$, HONO, $HNO_2$, SO, $SO_3$, $H_2SO_4$, $Cl_2$, ClO, $Cl_2O_2$, HOCl, $PH_3$, OCS, HI, HF, HBr, $BCl_3$, and $CH_{4-x}Cl_x$, where x equals 1 or 2.

5. The method of claim 4 wherein said corrosive gas comprises HCl.

6. The method of claim 1 wherein said gaseous species comprises water.

7. The method of claim 5 wherein said gaseous species comprises water and said selected spectral region is selected from the wavelength region between about 1420 and 1440 nanometers.

8. The method of claim 7 wherein said selected spectral region is selected from the wavelength region between about 1420 and 1434 nanometers.

9. The method of claim 7 wherein said selected spectral region is selected from the wavelength region between about 1433 and 1440 nanometers.

10. A gas detection system for detecting the presence of gaseous species in a gas sample containing corrosive gas, comprising:
    (a) a laser cavity;
    (b) a gain medium which resides therein, said gain medium outputting light having a wavelength distribution at least a portion of which is in a spectral region wherein:
        (i) said gaseous species has at least one absorption feature, and
        (ii) said corrosive gas has essentially no interfering absorption features;
    (c) a gas sample cell having windows which are transparent to light in said spectral region such that a beam of light can pass through said gas sample cell, said gas sample cell being contained in said laser such that light output from said gain medium passes through said gas sample cell prior to exiting said laser cavity;
    (d) means for inserting said gas sample containing said corrosive gas in said gas sample cell such that said light output from said gain medium passes through said gas sample prior to exiting said laser cavity;
    (e) means for sealing said gas sample within said gas sample cell such that said corrosive gas does not react with said laser cavity or said gain medium; and
    (f) a detector assembly for determining the presence and/or concentration of said gaseous species in said gas sample, said light output from said laser being directed to said detector assembly.

11. The gas detection system of claim 10 wherein said gain medium comprises an ion-doped crystal.

12. The gas detection system of claim 11 wherein said gain medium is pumped by a pump laser selected from the group consisting of a solid state crystal laser and a diode laser.

13. The gas detection system of claim 10 wherein said laser cavity is contained within a chamber configured to be evacuated of said gaseous species to be detected.

14. The gas detection system of claim 10 wherein said gas sample is contained in a region of said laser cavity which is astigmatically compensated to reduce astigmatism in said light output from said gain medium.

15. The gas detection system of claim 10 wherein said corrosive gas comprises gas selected from the group consisting of HCl, $N_2O$, NO, $NO_2$, HONO, $HNO_2$, SO, $SO_3$, $H_2SO_4$, $Cl_2$, ClO, $Cl_2O_2$, HOCl, $PH_3$, OCS, HI, HF, HBr, $BCl_3$, and $CH_{4-x}Cl_x$, where x equals 1 or 2.

16. The gas detection system of claim 15 wherein said corrosive gas comprises HCl.

17. The gas detection system of claim 10 wherein said gaseous species comprises water.

18. The gas detection system of claim 16 wherein said gaseous species comprises water and said spectral region is selected from the wavelength region consisting of the wavelength region between about 1420 and 1440 nanometers.

* * * * *